United States Patent
Wiesel et al.

(10) Patent No.: US 12,011,436 B2
(45) Date of Patent: Jun. 18, 2024

(54) USE OF NOX INHIBITORS FOR TREATMENT OF CANCER

(71) Applicants: CALLIDITAS THERAPEUTICS SUISSE SA, Plan-les-Ouates (CH); UNIVERSITY OF SOUTHAMPTON, Southampton (GB)

(72) Inventors: Philippe Wiesel, Paris (FR); Freddy Heitz, Bernex (CH); Gareth Thomas, Burley (GB); Christopher Hanley, Southampton (GB); Kirsty Ford, Weymouth (GB)

(73) Assignees: CALLIDITAS THERAPEUTICS SUISSE SA, Plan-les-Ouates (CH); UNIVERSITY OF SOUTHAMPTON, Southamptom (GB)

( * ) Notice: Subject to any disclaimer, the term of this patent is extended or adjusted under 35 U.S.C. 154(b) by 368 days.

(21) Appl. No.: 16/760,910

(22) PCT Filed: Nov. 1, 2018

(86) PCT No.: PCT/EP2018/079945
§ 371 (c)(1),
(2) Date: May 1, 2020

(87) PCT Pub. No.: WO2019/086579
PCT Pub. Date: May 9, 2019

(65) Prior Publication Data
US 2021/0177811 A1   Jun. 17, 2021

(30) Foreign Application Priority Data
Nov. 1, 2017   (EP) .................... 17199601

(51) Int. Cl.
| | |
|---|---|
| *A61K 31/437* | (2006.01) |
| *A61K 31/4025* | (2006.01) |
| *A61K 31/5377* | (2006.01) |
| *A61K 35/17* | (2015.01) |
| *A61K 38/19* | (2006.01) |
| *A61K 39/00* | (2006.01) |
| *A61K 39/245* | (2006.01) |
| *A61K 39/395* | (2006.01) |
| *A61P 35/00* | (2006.01) |

(52) U.S. Cl.
CPC ........ *A61K 31/437* (2013.01); *A61K 31/4025* (2013.01); *A61K 31/5377* (2013.01); *A61K 35/17* (2013.01); *A61K 38/191* (2013.01); *A61K 39/245* (2013.01); *A61K 39/3955* (2013.01); *A61P 35/00* (2018.01); *A61K 2039/505* (2013.01); *A61K 2039/507* (2013.01)

(58) Field of Classification Search
CPC .............. A61K 31/437; A61K 31/4025; A61K 31/5377; A61K 35/17; A61K 38/191; A61K 39/245; A61K 39/3955; A61K 2039/505; A61K 2039/507; A61K 31/4439; A61K 31/444; A61K 31/4725; A61K 31/551; A61K 2300/00; A61P 35/00

See application file for complete search history.

(56) References Cited

U.S. PATENT DOCUMENTS

| | | |
|---|---|---|
| 3,931,407 A | 1/1976 | Richard et al. |
| 4,909,827 A | 3/1990 | Gehring et al. |
| 5,869,516 A | 2/1999 | Arlt et al. |
| 6,107,306 A | 8/2000 | Carpino et al. |
| 6,624,309 B1 | 9/2003 | Lloyd et al. |
| 8,288,432 B2 | 10/2012 | Page et al. |
| 8,389,518 B2 | 3/2013 | Page et al. |
| 8,404,742 B2 | 3/2013 | Wierzbicki et al. |
| 8,455,485 B2 | 6/2013 | Page et al. |
| 8,455,486 B2 | 6/2013 | Page et al. |
| 8,481,562 B2 | 7/2013 | Page et al. |
| 8,748,456 B2 | 6/2014 | Page et al. |
| 8,865,758 B2 | 10/2014 | Page et al. |
| 8,940,760 B2 | 1/2015 | Page et al. |
| 9,006,238 B2 | 4/2015 | Page et al. |
| 9,012,449 B2 | 4/2015 | Page et al. |
| 9,073,919 B2 | 7/2015 | Page et al. |
| 9,096,588 B2 | 8/2015 | Page et al. |
| 9,351,988 B2 | 5/2016 | Ruiz Altaba et al. |
| 9,394,306 B2 | 7/2016 | Page et al. |
| 9,974,791 B2 | 5/2018 | Page et al. |
| 10,130,619 B2 | 11/2018 | Machin et al. |
| 10,772,891 B2 | 9/2020 | Page et al. |

(Continued)

FOREIGN PATENT DOCUMENTS

| | | |
|---|---|---|
| DE | 102005048897 | 10/2005 |
| EP | 0274642 A | 7/1988 |

(Continued)

OTHER PUBLICATIONS

Hanley, et al., JNCI J Natl Cancer Inst 2018 100(1); Published online Aug. 3, 2017 (Year: 2018).*
Hanley (Hanley, et al., Journal of National Cancer Institute, 2018, 110:109-120; Published online: Aug. 3, 2017).*
MMehra, et al., Journal of Clinical Oncology, 2016, 34:6012.*
Zhang, et al., Blood. 2009, 114:1545-1552.*
Jayavelu, et al., Leukemia, 2016, 30:473-483.*
US Clinical Trial Identifier: NCT02768792; First posted: May 11, 2016.*
Hsieh, et al., PLoS ONE (2011) 6(9): e23945 (Year: 2011).*
Altenhofer, et al., Antioxidants and Redox Signaling (2015) 22:406 (Year: 2015).*
Reardon, et al., Neuro-Oncology (2016) 18:ATIM-35 (Year: 2016).*
Meitzler, et al., Redox Biology (2017) 13:182 (Year: 2017).*

(Continued)

*Primary Examiner* — Julie Wu
*Assistant Examiner* — John L Van Druff
(74) *Attorney, Agent, or Firm* — Troutman Pepper Hamilton Sanders LLP

(57) ABSTRACT

The present invention is related to compounds, methods, compositions and uses that are able to restore responsiveness to immunotherapy, in particular immune check point inhibitors or anti-cancer vaccine or to anti-angiogenesis treatment.

12 Claims, 8 Drawing Sheets

(56) References Cited

U.S. PATENT DOCUMENTS

| | | | |
|---|---|---|---|
| 2007/0004626 | A1 | 1/2007 | Masuda et al. |
| 2007/0014739 | A1 | 1/2007 | Eldridge et al. |
| 2007/0037883 | A1 | 2/2007 | Dusting et al. |
| 2007/0082910 | A1 | 4/2007 | Yamamoto et al. |
| 2008/0076778 | A1 | 3/2008 | Ossovskaya et al. |
| 2008/0176934 | A1 | 7/2008 | Verbeuren et al. |
| 2009/0099179 | A1 | 4/2009 | Klein et al. |
| 2009/0163452 | A1 | 6/2009 | Schwartz |
| 2014/0323500 | A1 | 10/2014 | Brandes et al. |

FOREIGN PATENT DOCUMENTS

| | | |
|---|---|---|
| EP | 1175900 A2 | 1/2002 |
| EP | 1 291 017 | 3/2003 |
| EP | 1396493 | 3/2004 |
| EP | 1505068 | 2/2005 |
| EP | 2002835 A | 12/2008 |
| EP | 2 165 707 | 3/2010 |
| EP | 2 166 010 | 3/2010 |
| WO | WO 97/19679 | 6/1997 |
| WO | WO 2002/088122 | 11/2002 |
| WO | WO 2004/005267 | 1/2004 |
| WO | WO 2005/080378 | 9/2005 |
| WO | WO 2006/041874 | 4/2006 |
| WO | WO 2006/094187 | 9/2006 |
| WO | WO 2008/063514 | 5/2008 |
| WO | WO 2008/113856 | 9/2008 |
| WO | WO 08/116926 | 10/2008 |
| WO | WO 2009/072643 | 6/2009 |
| WO | WO 2010/035217 | 4/2010 |
| WO | WO 2010/035219 | 4/2010 |
| WO | WO 2010/035220 | 4/2010 |
| WO | WO 2010/035221 | 4/2010 |
| WO | WO 2011/036651 | 3/2011 |
| WO | WO 2011/085293 | 7/2011 |
| WO | WO 2011/101804 | 8/2011 |
| WO | WO 2011/101805 | 8/2011 |
| WO | WO 2013/068972 | 5/2013 |
| WO | WO 2015/049655 | 4/2015 |
| WO | WO 2016/098005 | 6/2016 |
| WO | WO 2016/207785 | 12/2016 |

OTHER PUBLICATIONS

Merck, et al. US Clinical Trial NCT02564263; First posted Sep. 30, 2015 (Year: 2015).*

Chen, et al., Oxidative Medicine and Cellular Longevity (2016), Article ID: 1580967 (Year: 2016).*

Merck, et al. US Clinical Trial NCT02564263; Version 1: Sep. 29, 2015 (Year: 2015).*

Abdelrahman, M. et al. "Inhibitors of NADPH Oxidase Reduce the Organ Injury in Hemorrhagic Shock" *Shock*, 2005, pp. 107-114, vol. 23, No. 2.

Abdulmahdi, W. et al. "Kidney dysfunction in the low-birth weight murine adult: implications of oxidative stress" *Am J Physiol Renal Physiol.*, 2018, pp. F583-F594, vol. 315.

ACS on STN Tokyo, Registry, RN=955327-56-7 (Nov. 21, 2007), 955327-53-4 (Nov. 21, 2007), 955327-50-1 (Nov. 21, 2007), 955327-47-6 (Nov. 21, 2007), 955327-44-3 (Nov. 21, 2007), 955285-61-7 (Nov. 21, 2007), 955285-55-9 (Nov. 21, 2007), 955285-49-1 (Nov. 21, 2007), 955265-43-5 (Nov. 21, 2007), 955272-06-7 (Nov. 21, 2007), 955285-37-7 (Nov. 21, 2007) pp. 1-6.

Altenhofer, S. et al. "The NOX toolbox: validating the role of NADPH oxidases in physiology and disease" *Cellular and Molecular Life Sciences*, 2012, pp. 2327-2343, vol. 69.

Anantharam, V. et al. "Pharmacological inhibition of neuronal NADPH oxidase protects against 1-methyl-4-phenylpyridinium (MPP+)-induced oxidative stress and apoptosis in mesencephalic dopaminergic neuronal cells" *Neuro Toxicology*, 2007, pp. 988-997, vol. 28.

Aoyama, T. et al. "Nicotinamide Adenine Dinucleotide Phosphate Oxidase in Experimental Liver Fibrosis: GKT137831 as a Novel Potential Therapeutic Agent" *Hepatology*, 2012, pp. 2316-2327, vol. 56, No. 6.

Appukuttan, B. et al. "Effect of NADPH oxidase 1 and 4 blockade in activated human retinal endothelial cells" *Clinical and Experimental Ophthalmology*, 2018, pp. 652-660, vol. 46.

Asaba, K. et al. "Effects of NADPH oxidase inhibitor in diabetic nephropathy" *Kidney International*, 2005, pp. 1890-1898, vol. 67.

Asensio-López, M. C. et al. "Early oxidative damage induced by doxorubicin: Source of production, protection by GKT137831 and effect on $Ca^{2+}$ transporters in HL-1 cardiomyocytes" *Archives of Biochemistry and Biophysics*, 2016, pp. 26-36, vol. 594.

Babalola, O. et al. "NADPH Oxidase Enzymes in Skin Fibrosis: Molecular Targets and Therapeutic Agents" *Archives of Dermatological Research*, May 2014, pp. 313-330, vol. 306, No. 4.

Baker, M. A. et al. "Reactive oxygen species in spermatozoa: methods for monitoring and significance for the origins of genetic disease and infertility" *Reproductive Biology and Endocrinology*, 2005, pp. 1-9, vol. 3, No. 67.

Banfi, B. et al. "NOX3, a Superoxide-generating NADPH Oxidase of the Inner Ear" *The Journal of Biological Chemistry*, Oct. 29, 2004, pp. 46065-46072, vol. 279, No. 44.

Bao, X. et al. "Atorvastatin inhibits homocysteine-induced oxidative stress and apoptosis in endothelial progenitor cells involving Nox4 and p38MAPK" *Atherosclerosis*, 2010, pp. 114-121, vol. 210.

Barnett, R. M. et al. "Targeted Therapy for Cancer-Associated Fibroblasts: Are We There Yet?" *Journal of the National Cancer Institute*, 2018, pp. 1-3, vol. 110, No. 1.

Barman, S. A. et al. "NADPH Oxidase 4 Is Expressed in Pulmonary Artery Adventitia and Contributes to Hypertensive Vascular Remodeling" *Arteriosclerosis, Thrombosis, and Vascular Biology*, Jun. 19, 2014, pp. 1-24, vol. 34.

Baumer, A. T. et al. "The NAD(P)H Oxidase Inhibitor Apocynin Improves Endothelial NO/Superoxide Balance and Lowers Effectively Blood Pressure in Spontaneously Hypertensive Rats: Comparison to Calcium Channel Blockade" *Clinical and Experimental Hypertension*, 2007, pp. 287-299, vol. 29.

Bedard, K. et al. "The NOX Family of ROS-Generating NADPH Oxidases: Physiology and Pathophysiology" *Physiological Reviews*, Jan. 2007, pp. 245-313, vol. 87.

Bernard, K. et al. "NADPH Oxidase 4 (Nox4) Suppresses Mitochondrial Biogenesis and Bioenergetics in Lung Fibroblasts via a Nuclear Factor Erythroid-Derived 2-like 2 (Nrf2)-Dependent Pathway" *Journal of Biological Chemistry*, Jan. 3, 2017, pp. 1-22.

Bettaieb, A. et al. "Hepatocyte Nicotinamide Adenine Dinucleotide Phosphate Reduced Oxidase 4 Regulates Stress Signaling, Fibrosis, and Insulin Sensitivity During Development of Steatohepatitis in Mice" *Gastroenterology*, 2015, pp. 468-480, vol. 149, No. 2, Supplemental Material pp. 480.e1-480.e10.

Block, K. et al. "Subcellular localization of Nox4 and regulation in diabetes" *PNAS*, Aug. 25, 2009, pp. 14385-14390, vol. 106, No. 34.

Bone Health and Osteoporosis A Report of the Surgeon General (Chapters 2 and 3), U.S. Department of Health and Human Services Public Health Service Office of the Surgeon General, 2004, pp. 1-53.

Borbely, G. et al. "Small-Molecule Inhibitors of NADPH Oxidase 4" *J. Med. Chem.*, 2010, pp. 6758-6762, vol. 53.

Brigham, K. L. "Role of Free Radicals in Lung Injury" *Chest*, Jun. 1986, pp. 859-863, vol. 89, No. 6.

Briones, A. M. et al. "Differential regulation of Nox1, Nox2 and Nox4 in vascular smooth muscle cells from WKY and SHR" *Journal of the American Society of Hypertension*, 2011, pp. 137-153, vol. 5, No. 3.

Buck, T. et al. "The NADPH oxidase 4 is a major source of hydrogen peroxide in human granulosa-lutein and granulosa tumor cells" *Scientific Reports*, Mar. 2019, pp. 1-11, vol. 9.

Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.

Camargo, L. L. et al. "Vascular Nox compartmentalization, protein hyperoxidation and ER stress response in hypertension" *Hypertension*, Jul. 2018, pp. 1-22, vol. 72, No. 1.

(56) References Cited

OTHER PUBLICATIONS

Cancer [online], retrieved on Jul. 6, 2007, retrieved from the internet, URL: http://www.nim.nih.gov/medlineplus/cancer.html, pp. 1-10.

Carpino, P. et al. "Discovery and Biological Characterization of Capromorelin Analogues with Extended Half-Lives" *Bioorganic & Medicinal Chemistry Letters*, Nov. 18, 2002, pp. 3279-3282, vol. 12, No. 22.

Carpino, P. et al. "Pyrazolinone-piperidine Dipeptide Growth Hormone Secretagogues (GHSs): Discovery of Capromorelin" *Bioorganic & Medicinal Chemistry*, Feb. 20, 2003, pp. 581-590, vol. 11, No. 4.

Cayatte, A. J. et al. "S17834, a New Inhibitor of Cell Adhesion and Atherosclerosis That Targets NADPH Oxidase" *Arteriosclerosis, Thrombosis, and Vascular Biology*, 2001, pp. 1577-1584, vol. 21.

Cha, J. J. et al. "APX-115, a first-in-class pan-NADPH oxidase (Nox) inhibitor, protects db/db mice from renal injury" *Laboratory Investigation*, 2017, pp. 1-13.

Chabner, B. A. et al. "Chemotherapy and the war on cancer" *Nature Reviews Cancer*, Jan. 2005, pp. 65-72, vol. 5.

Chan, E. C. et al. "Regulation of cell proliferation by NADPH oxidase-mediated signaling: Potential roles in tissue repair, regenerative medicine and tissue engineering" *Pharmacology & Therapeutics*, 2009, pp. 97-108, vol. 122.

Chang, G. et al. "Specific Inhibition of NADP(H) Oxidase (NOX) Abrogates the Tumorigenic Phenotype of Renal Cancer Cells" Poster at Annual Meeting of the Society of Basic Urology, Nov. 2009, New Orleans, USA, p. 1.

Chemcats Accession No. 2029347921, Jun. 13, 2008, XP-002514328, p. 1.

Chemcats Accession No. 2049339652, Jun. 13, 2008, XP-002514424, pp. 1-6.

Chen, J.-R. et al. "Inhibition of NADPH Oxidases Prevents Chronic Ethanol-Induced Bone Loss in Female Rats" *The Journal of Pharmacology and Experimental Therapeutics*, Mar. 2011, pp. 734-742, vol. 336, No. 3.

Chen, P. et al. "Role of NADPH oxidase and ANG II in diabetes-induced retinal leukostasis" *Am. J. Physiol. Reul. Integr. Comp. Physiol.*, 2007, pp. R1619-R1629, vol. 293.

Chen, L. et al. "Critical role of X-box binding protein 1 in NADPH oxidase 4-triggered cardiac hypertrophy is mediated by receptor interacting protein kinase 1" *Cell Cycle*, Dec. 8, 2016, pp. 348-359, vol. 16, No. 4.

Cheng, A. J. et al. "Antioxidant treatments do not improve force recovery after fatiguing stimulation of mouse skeletal muscle fibres" *The Journal of Physiology*, 2015, pp. 457-472, vol. 593, No. 2.

Cheng, G. et al. "Homologs of gp91phox: cloning and tissue expression of Nox3, Nox4, and Nox5" *Gene*, 2001, pp. 131-140, vol. 269.

Chirino, Y. I. et al. "Protective effects of apocynin against cisplatin-induced oxidative stress and nephrotoxicity" *Tosicology*, 2008, pp. 18-23, vol. 245.

Cho, S. et al. "NADPH oxidase 4 mediates TGF-β1/Smad signaling pathway induced acute kidney injury in hypoxia" *PLOS ONE*, Jul. 18, 2019, pp. 1-20.

Choi, D.-H. et al. "Matrix Metalloproteinase-3 Causes Dopaminergic Neuronal Death through Nox1-Regenerated Oxidative Stress" *PLoS ONE*, Dec. 23, 2014, pp. 1-25.

Cucoranu, I. et al. "NAD(P)H Oxidase 4 Mediates Transforming Growth Factor-b1-Induced Differentiation of Cardiac Fibroblasts Into Myofibroblasts" *Circulation Research*, 2005, pp. 900-907, vol. 97.

Cui, Y. et al. "The Nox1/Nox4 inhibitor attenuates acute lung injury induced by ischemia-reperfusion in mice" *PLOS ONE*, Dec. 20, 2018, pp. 1-15.

Dachert, J. et al. "Targeting ferroptosis in rhabdomyosarcoma cells" *Int J Cancer*, Jan. 2020, pp. 1-40.

Database CA [Online], Chemical Abstract Accession No. 1977:155590, Ozdowska, Z. "New derivatives of N-benzyl-4-carbethoxy-3-piperidone" *Roczniki Chemii*, 1976, pp. 1-2, vol. 50, No. 10, XP-002598501.

Database CA [Online] Chemical Abstracts Service, Accession No. 2007:341007, 2007, XP-002558729, p. 1.

Database CA [Online] Chemical Abstracts Service, Accession No. 2004:14711, 2003, XP-002558730, pp. 1-2.

Deliyanti, D. et al. "Inhibition of Nox1/4 with GKT137831: a potential novel treatment to attenuate neuroglial cell inflammation in the retina" *Journal of Neuroinflammation*, 2015, pp. 1-13, vol. 12, No. 136.

De Minicis, S. et al. "Oxidative stress in alcoholic liver disease: Role of NADPH oxidase complex" *Journal of Gastroenterology and Hepatology*, 2008, pp. S98-S103, Supp 1, No. 23.

De Minicis, S. et al. "NOX in liver fibrosis" *Archives of Biochemistry and Biophysics*, 2007, pp. 266-272, vol. 462.

Deng, W. et al. "NADPH oxidase 1/4 inhibition attenuates the portal hypertensive syndrome via modulation of mesenteric angiogenesis and arterial hyporeactivity in rats" *Clinics and Research in Hepatology and Gastroenterology*, 2019, pp. 255-265, vol. 43.

"Derivative." Merriam-Webster Online Dictionary, 2010, accessed Apr. 20, 2010, http://merriam-webster.com/dictionary/derivative.

Di Marco, E. et al. "Pharmacological inhibition of NOX reduces atherosclerotic lesions, vascular ROS and immune-inflammatory responses in diabetic Apoe -/- mice" *Diabetologia*, 2014, pp. 633-642, vol. 57.

Di Marco, E. et al. "NOX4-derived reactive oxygen species limit fibrosis and inhibit proliferation of vascular smooth muscle cells in diabetic atherosclerosis" *Free Radical Biology and Medicine*, 2016, pp. 556-567, vol. 97.

Dixon, S. J. et al. "Ferroptosis: An Iron-Dependent Form of Nonapoptotic Cell Death" *Cell*, May 25, 2012, pp. 1060-1072, vol. 149.

Djordjevic, T. et al. "Human Urotensin II Is a Novel Activator of NADPH Oxidase in Human Pulmonary Artery Smooth Muscle Cells" *Arteriosclerosis, Thrombosis, and Vascular Biology*, Mar. 2005, pp. 519-525, vol. 25.

Dornow, A. et al. "Darstellung and Umsetzung einiger substituierter 3-Nitro-pyridine" *Chem. Ber.*, 1966, pp. 244-253, vol. 99.

Eid, S. A. et al. "Targeting the NADPH Oxidase-4 and Liver X Receptor Pathway Preserves Schwann Cell Integrity in Diabetic Mice" *Diabetes*, Mar. 2020, pp. 448-464, vol. 69.

El Benna, J. et al. "NADPH Oxidase Priming and p47phox Phosphorylation in Neutrophils from Synovial Fluid of Patients with Rheumatoid Arthritis and Spondylarthropathy" *Inflammation*, Dec. 2002, pp. 273-278, vol. 26, No. 6.

Ellis, E. A. et al. "Increased $H_2O_2$, Vascular Endothelial Growth Factor and Receptors in the Retina of the BBZ/WOR Diabetic Rat" *Free Radical Biology & Medicine*, 2000, pp. 91-191, vol. 28, No. 1.

Ellis, E. A. et al. "Time Course of NADH Oxidase, Inducible Nitric Oxide Synthase and Peroxynitrite in Diabetic Retinopathy in the BBZ/WOR Rat" *Nitric Oxide: Biology and Chemistry*, 2002, pp. 295-304, vol. 6, No. 3.

Englert, S. M. et al. "Pyrazolones Derived from the Carbethoxypiperidones" *Journal of American Chemical Society*, Mar. 1934, pp. 700-702, vol. 56.

Ferrara, N. et al. "Angiogenesis as a therapeutic target" *Nature*, Dec. 15, 2005, pp. 967-974, vol. 438.

Folkman, J. "Angiogenesis" *Annu. Rev. Med.*, 2006, pp. 1-18, vol. 57.

Forbes, J. M. et al. "Diabetic Nephropathy: Where Hemodynamics Meets Metabolism" *Exp Clin Endocrinol Diabetes*, 2007, pp. 1-16.

Freedman, M. S. et al. "Treatment Optimization in Multiple Sclerosis" *Canadian Journal of Neurological Sciences*, 2004, pp. 157-168, vol. 31.

Fujita, M. et al. "Pyrroloquinolones and pyrazoloquinolones as potential antibacterial agents. Synthesis and antibacterial activity" *European Journal of Medicinal Chemistry*, 1996, pp. 981-988, vol. 31.

Fukuyama, M. et al. "Overexpression of a novel superoxide-producing enzyme, NADPH oxidase 1, in adenoma and well differentiated adenocarcinoma of the human colon" *Cancer Letters*, 2005, pp. 97-104, vol. 221.

Garrido-Urbani, S. et al. "Targeting Vascular NADPH Oxidase 1 Blocks Tumor Angiogenesis through a PPARα Mediated Mechanism" *PLoS ONE*, Feb. 2011, pp. 1-13, vol. 6, Issue 2.

(56) References Cited

OTHER PUBLICATIONS

Gavazzi, G. et al. "NOX1 Deficiency Protects from Aortic Dissection in Response to Angiotensin II" *Hypertension*, 2007, pp. 189-196, vol. 50.
Geis, C. et al. "NOX4 is an early initiator of neuropathic pain" *Experimental Neurology*, 2017, pp. 94-103, vol. 288.
Girouard, H. et al. "Neurovascular coupling in the normal brain and in hypertension, stroke, and Alzheimer disease" *Journal of Applied Physiology*, 2006, pp. 328-335, vol. 100.
Goettsch, C. et al. "NADPH oxidase 4 limits bone mass by promoting osteoclastogenesis" *The Journal of Clinical Investigation*, Nov. 2013, pp. 4731-4738, vol. 123, No. 11.
Golub, T. R. et al. "Molecular Classification of Cancer: Class Discovery and Class Prediction by Gene Expression Monitoring" *Science*, Oct. 15, 1999, pp. 531-537, vol. 286.
Gorin, Y. et al. "Targeting NADPH oxidase with a novel dual Nox1/Nox4 inhibitor attenuates renal pathology in type 1 diabetes" *Am J Physiol Renal Physiol*, Feb. 5, 2015, pp. F1276-F1287, vol. 308.
Gorin, Y. et al. "Nox4 NAD(P)H Oxidase Mediates Hypertrophy and Fibronectin Expression in the Diabetic Kidney" *The Journal of Biological Chemistry*, Nov. 25, 2005, pp. 39616-39626, vol. 280, No. 47.
Gray, S. P. et al. "Combined NOX1/4 inhibition with GKT137831 in mice provides dose-dependent reno- and atheroprotection even in established micro- and macrovascular disease" *Diabetologia*, Feb. 3, 2017, pp. 1-11.
Gray, S. P. et al. "NADPH Oxidase 1 Plays a Key Role in Diabetes Mellitus-Accelerated Atherosclerosis" *Circulation*, May 7, 2013, pp. 1888-1902.
Green, D. E. et al. "The Nox4 Inhibitor GKT137831 Attenuates Hypoxia-Induced Pulmonary Vascular Cell Proliferation" *American Journal of Respiratory Cell and Molecular Biology*, Nov. 2012, pp. 718-726, vol. 47, Issue 5.
Griendling, K. K. et al. "NAD(P)H Oxidase: Role in Cardiovascular Biology and Disease" *Circulation Research*, 2000, pp. 494-501, vol. 86.
Guichard, C. et al. "NOX family NADPH oxidases in liver and in pancreatic islets: a role in the metabolic syndrome and diabetes?" *Biochemical Society Transactions*, 2008, pp. 920-929, vol. 36.
Guillou, S. et al. "N-arylation of 3-alkoxypyrazoles, the case of the pyridines" *Tetrahedron*, Feb. 10, 010, pp. 2654-2663, vol. 66, No. 14.
Gukovskaya, A. S. et al. "Neutrophils and NADPH Oxidase Mediate Intrapancreatic Trypsin Activation in Murine Experimental Acute Pancreatitis" *Gastroenterology*, 2002, pp. 974-984, vol. 122.
Hausmann, M. et al. "Subtractive screening reveals up-regulation of NADPH oxidase expression in Crohn's disease intestinal macrophages" *Clin. Exp. Immunol.*, 2001, pp. 48-55, vol. 125.
Hecker, L. et al. "Reversal of Persistent Fibrosis in Aging by Targeting Nox4-Nrf2 Redox Imbalance" *Sci Transl Med*, Apr. 9, 2014, pp. 1-12, vol. 6, No. 231.
Heidi Wan, W.-Y. et al. "NADPH Oxidase-4 Overexpression Is Associated With Epithelial Ciliary Dysfunction in Neutrophilic Asthma" *Chest*, 2016, pp. 1445-1459, vol. 149, No. 6.
Helmcke, I. et al. "Identification of Structural Elements in Nox1 and Nox4 Controlling Localization and Activity" *Antioxidants & Redox Signaling*, 2009, pp. 1279-1287, vol. 11, No. 6.
Hirschhäuser, C. et al. "NOX4 in Mitochondria: Yeast Two-Hybrid-Based Interaction with Complex I Without Relevance for Basal Reactive Oxygen Species" *Antioxidants & Redox Signaling*, 2015, pp. 1-7.
Hoidal, J. R. et al. "The Role of Endogenous NADPH Oxidases in Airway and Pulmonary Vascular Smooth Muscle Function" *Antioxidants & Redox Signaling*, 2003, pp. 751-758, vol. 5.
Hollins, F. et al. "Airway smooth muscle NOX4 is upregulated and modulates ROS generation in COPD" *Respiratory Research*, 2016, pp. 1-5, vol. 17, No. 84.
Hosseini, M. et al. "Premature Skin Aging Features Rescued by Inhibition of NADPH Oxidase Activity in XPC-Deficient Mice" *Journal of Investigative Dermatology*, Jan. 15, 2015, pp. 1108-1118, vol. 135.
Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.
Hua, C. et al. "The vascular NAD(P)H oxidases as therapeutic targets in cardiovascular diseases" *TRENDS in Pharmacological Sciences*, Sep. 2003, pp. 471-478, vol. 24, No. 9.
Huang, W. et al. "Simvastatin protects osteoblast against $H_2O_2$-induced oxidative damage via inhibiting the upregulation of Nox4" *Mol Cell Biochem*, 2012, pp. 71-77, vol. 360.
Inoguchi, T. et al. "NAD(P)H Oxidase Activation: A Potential Target Mechanism for Diabetic Vascular Complications, Progressive β-Cell Dysfunction and Metabolic Syndrome" *Current Drug Targets*, 2005, pp. 495-501, vol. 6.
Jain, V. K. et al. "NADPH Oxidase and Myeloperoxidase Activity in Psoriasis Leukocytes" *The Journal of Dermatology*, 1985, pp. 425-428, vol. 12.
Jarman, E. R. et al. "An inhibitor of NADPH oxidase-4 attenuates established pulmonary fibrosis in a rodent disease model" *AJRCMB Articles in Press*, Aug. 26, 2013, pp. 1-30.
Jayavelu, A. K. et al. "NOX4-driven ROS formation mediates PTP inactivation and cell transformation in FLT3ITD-positive AML cells" *Leukemia*, 2016, pp. 473-483, vol. 30.
Jeong, B. Y. et al. "TGF-β-mediated NADPH oxidase 4-dependent oxidative stress promotes colistin-induced acute kidney injury" *J Antimicrob Chemother.*, 2018, pp. 962-972, vol. 73.
Jeong, B. Y. et al. "Oxidative stress caused by activation of NADPH oxidase 4 promotes contrast-induced acute kidney injury" *PLOS ONE*, Jan. 12, 2018, pp. 1-22, vol. 13, No. 1.
Jha, J. et al. "Genetic Targeting or Pharmacologic Inhibition of NADPH Oxidase Nox4 Provides Renoprotection in Long-Term Diabetic Nephropathy" *J Am Soc Nephrol*, 2014, pp. 1-18, vol. 25.
Jiang, J. et al. "Apoptotic body engulfment by hepatic stellate cells promotes their survival by the JAK/STAT and Akt/NF-κB-dependent pathways" *J Hepatol.*, Jul. 2009, pp. 139-148, vol. 51. No. 1.
Jiang, J. X. et al. "Liver fibrosis and hepatocyte apoptosis are attenuated by GKT137831, a novel NOX4/NOX1 inhibitor in vivo" *Free Radical Biology and Medicine*, 2012, pp. 289-296, vol. 53.
Jiao, W. et al. "Activation of the Notch-Nox4-reactive oxygen species signaling pathway induces cell death in high glucose-treated human retinal endothelial cells" *Molecular Medicine Reports*, 2019, pp. 667-677, vol. 19.
Jin, L. et al. "NADPH oxidase: recent evidence for its role in erectile dysfunction" *Asian J. Androl.*, Jan. 2008, pp. 6-13, vol. 10.
Junker, L. M. et al. "High-Throughput Screens for Small-Molecule Inhibitors of *Pseudomonas aeruginosa* Biofilm Development" *Antimicrobial Agents and Chemotherapy*, Oct. 2007, pp. 3582-3590, vol. 51, No. 10.
Kakehi, T. et al. "NOX enzymes and diabetic complications" *Semin Immunopathol*, 2008, pp. 301-314, vol. 30.
Kawai, Y. et al. "Relationship of Intracellular Calcium and Oxygen Radicals to Cisplatin-Related Renal Cell Injury" *J. Pharmacol. Sci.*, 2006, pp. 65-72, vol. 100.
Kerbel, R. S. "Tumor Angiogenesis" *N. Engl J Med*, May 8, 2008, pp. 2039-2049, vol. 358.
Kim, J.-E. et al. "NADPH Oxidase inhibitors: a patent review" *Expert Opinion of Therapeutic Patents*, Aug. 2011, pp. 1147-1158, vol. 21, No. 8.
Kim, H. J. et al. "Role of muscular eNOS in skeletal arteries: endothelium-independent hypoxic vasoconstriction of the femoral artery is impaired in eNOS-deficient mice" *Am J Physiol Cell Physiol*, 2016, pp. C508-C517, vol. 311.
Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.
Klein, C. et al. CAS:147:427219, 2007, Accession No. 2007:1146277, pp. 1-4.

(56) References Cited

OTHER PUBLICATIONS

Krehan, D. et al. "Aza-THIP and Related Analogues of THIP as GABAc Antagonists" *Bioorganic & Medicinal Chemistry*, Jan. 1, 2003, pp. 4891-4896, vol. 11.

Krijnen, P. A. et al. "Increased Nox2 expression in human cardiomyocytes after acute myocardial infarction" *J. Clin. Pathol.*, 2003, pp. 194-199, vol. 56.

Lafeber, F. P. J. G. et al. "Apocynin, a plant-derived, cartilage-saving drug, might be useful in the treatment of rheumatoid arthritis" *Rheumatology*, 1999, pp. 1088-1093, vol. 38.

Lala, P. K. et al. "Role of nitric oxide in tumor progression: Lessons from experimental tumors" *Cancer and Metastasis Reviews*, 1998, pp. 91-106, vol. 17.

Laleu, B. et al. "First in Class, Potent, and Orally Bioavailable NADPH Oxidase Isoform 4 (Nox4) Inhibitors for the Treatment of Idiopathic Pulmonary Fibrosis" *Journal of Medicinal Chemistry*, 2010, pp. 7715-7730, vol. 53.

Lambeth, J. D. et al. "NOX enzymes as novel targets for drug development" *Semin Immunopathol*, 2008, pp. 1-25.

Lambeth, D. "Nox Enzymes, ROS, and Chronic Disease: An Example of Antagonistic Pleiotropy" *Free Radic Biol Med.*, Aug. 2007, pp. 332-347, vol. 43, No. 3.

Lan, T. et al. "Deficiency of NOX1 or NOX4 Prevents Liver Inflammation and Fibrosis in Mice through Inhibition of Hepatic Stellate Cell Activation" *PLoS One*, Jul. 29, 2015, pp. 1-19.

Lanone S. et al. "Bilirubin decreases NOS2 expression via inhibition of NAD(P)H oxidase: implications for protection against endotoxic shock in rats" *The FASEB Journal*, 2005, pp. 1-26.

Leaf, C. "The War on Cancer" *Fortune*, Mar. 9, 2004, pp. 1-26.

Lee, N. K. et al. "A crucial role for reactive oxygen species in RANKL-induced osteoclast differentiation" *Blood*, 2005, pp. 852-859, vol. 106.

Leto, T. L. et al. "Role of Nox Family NADPH Oxidases in Host Defense" *Antioxidants & Redox Signaling*, 2006, pp. 1549-1561, vol. 8, Nos. 9-10.

Li, H. et al. "Effect of Berberine on Bone Mineral Density in SAMP6 as a Senile Osteoporosis Model" *Biol. Pharm. Bull.*, 2003, pp. 110-111, vol. 26, No. 1.

Li, X. et al. "A critical role of the transient receptor potential melastatin 2 channel in a positive feedback mechanism for reactive oxygen species-induced delayed cell death" *J Cell Physiol.*, 2019, pp. 3647-3660, vol. 234.

Li, Y. et al. "Efficacy of Obcordata A from *Aspidopterys obcordata* on Kidney Stones by Inhibiting NOX4 Expression" *Molecules*, 2019, pp. 1-10, vol. 24.

Lindvall, O. et al. "Stem Cells for the treatment of neurological disorders" *Nature*, Jun. 29, 2006, pp. 1094-1096, vol. 441.

Liu, J. Q. et al. "Extracellular superoxide enhances 5-HT-induced murine pulmonary artery vasoconstriction" *American Journal of Physiology Lung Cellular and Molecular Physiology*, 2004, pp. L111-L118, vol. 287.

Liu, Y. et al. "Suppression of Microglial Inflammatory Activity by Myelin Phagocytosis: Role of p47-PHOX-Mediated Generation of Reactive Oxygen Species" *The Journal of Neuroscience*, Dec. 13, 2006, pp. 12904-12913, vol. 26, No. 50.

Lu, J. P. et al. "Androgens induce oxidative stress and radiation resistance in prostate cancer cells though NADPH oxidase" *Prostate Cancer and Prostatic Diseases*, 2010, pp. 39-46, vol. 13.

Lu, W. et al. "The role of the Nox4-derived ROS-mediated RhoA/Rho kinase pathway in rat hypertension induced by chronic intermittent hypoxia" *Sleep Breath*, 2017, pp. 667-677, vol. 21.

Lu, S. et al. "Hyperglycemia Acutely Increases Cytosolic Reactive Oxygen Species via O-linked GlcNAcylation and CaMKII Activation in Mouse Ventricular Myocytes" *Circulation Research*, 2020, pp. 1-18, Figures pp. 1-9.

Lu, G. et al. "Spironolactone suppresses aldosterone-induced Kv1.5 expression by attenuating mineralocorticoid receptor-Nox1/2/4-mediated ROS generation in neonatal rat atrial myocytes" *Biochemical and Biophysical Research Communications*, 2019, pp. 1-6.

Lu, W. J. et al. "VAS2870 and VAS3947 attenuate platelet activation and thrombus formation via a NOX-independent pathway downstream of PKC" *Scientific Reports*, 2019, pp. 1-13, vol. 9.

Maruotti, N. et al. "Osteoclastogenesis and arthritis" *Clin Exp Med*, 2011, pp. 137-145, vol. 11.

Massip-Copiz, M. M. et al. "CFTR impairment upregulates c-Src activity through IL-1β autocrine signaling" *Archives of Biochemistry and Biophysics*, 2017, pp. 1-12, vol. 616.

Miao, H. et al. "Nociceptive Behavior Induced by Chemotherapeutic Paclitaxel and Beneficial Role of Antioxidative Pathways" *Physiol. Res.* 2019, pp. 491-500, vol. 68.

Montezano, A. C. et al. "NADPH Oxidase 5 Is a Pro-Contractile Nox Isoform and a Point of Cross-Talk for Calcium and Redox Signaling-Implications in Vascular Function" *Journal of the American Heart Association*, 2018, pp. 1-15, vol. 7, Supplemental Methods, pp. 1-15, Supplemental Material pp. 1-18.

Moon, J.-S. et al. "NOX4-dependent fatty acid oxidation promotes NLRP3 inflammasome activation in macrophages" *Nature Medicine*, Sep. 2016, pp. 1002-1012, vol. 22, No. 9, Online Methods pp. 1-3.

Musset, B. et al. "NOX5 in Human Spermatozoa" *The Journal of Biological Chemistry*, Mar. 16, 2012, pp. 9376-9388, vol. 287, No. 12.

Naime, A. C. A. et al. "Tumor necrosis factor alpha has a crucial role in increased reactive oxygen species production in platelets of mice injected with lipopolysaccharide" *Platelets*, May 11, 2019, pp. 1-6.

Nam, S. M. et al. "Effects of NADPH oxidase inhibitor on diabetic nephropathy in OLETF rats: The role of reducing oxidative stress in its protective property" *Diabetes Research and Clinical Practice*, 2009, pp. 176-182, vol. 83.

Neves, K. B. et al. "VEGFR (Vascular Endothelial Growth Factor Receptor) Inhibition Induces Cardiovascular Damage via Redox-Sensitive Processes" *Hypertension*, Apr. 2018, pp. 638-647, vol. 71.

Neves, K. B. et al. "Chemerin Regulates Crosstalk Between Adipocytes and Vascular Cells Through Nox" *Hypertension—AHA*, 2015, pp. 657-666, vol. 66, Supplemental Data pp. 1-17.

Nibali, L. et al. "NADPH oxidase (CYBA) and FcγR polymorphisms as risk factors for aggressive periodontitis" *J. Clin. Periodontol*, 2006, pp. 529-539, vol. 33.

Nishio, T. et al. "Activated hepatic stellate cells and portal fibroblasts contribute to cholestatic liver fibrosis in MDR2 knockout mice" *Journal of Hepatology*, 2019, pp. 573-585, vol. 71.

Nunomura, A. et al. "Oxidative Damage Is the Earliest Event in Alzheimer Disease" *Journal of Neuropathology and Experimental Neurology*, Aug. 2001, pp. 759-767, vol. 60, No. 8.

Padilla, J. et al. "TRAF3IP2 mediates high glucose-induced endothelin-1 production as well as endothelin-1-induced inflammation in endothelial cells" *Am J Physiol Heart Circ Physiol.*, 2018, pp. H52-H64, vol. 314.

Patel, C. et al. "Prolonged Reactive Oxygen Species Generation and Nuclear Factor-κB Activation after a High-Fat, High-Carbohydrate Meal in the Obese" *The Journal of Clinical Endocrinology & Metabolism*, 2007, pp. 4476-4479, vol. 92, No. 111.

Patel, M. et al. "Activation of NAPDH oxidase and extracellular superoxide production in seizure-induced hippocampal damage" *Journal of Neurochemistry*, 2005, pp. 123-131, vol. 92.

Peng, J.-J. et al. "Diabetic retinopathy: Focus on NADPH oxidase and its potential as therapeutic target" *European Journal of Pharmacology*, 2019, pp. 381-387, vol. 853.

Peters, E. A. et al. "Effect of Apocynin on Ozone-Induced Airway Hyperresponsiveness to Methacholine in Asthmatics" *Free Radical Biology & Medicine*, 2001, pp. 1442-1447, vol. 31, No. 11.

Piera-Velazquez, S. et al. "Increased Expression of NAPDH Oxidase 4 (NOX4) in Systemic Sclerosis Dermal Fibroblasts: Regulation by Transforming Growth Factor β" *Arthritis and Rheumatology*, 2015, pp. 1-30.

Pillarisetti, S. et al. "Role of oxidative stress and inflammation in the origin of Type 2 diabetes—a paradigm shift" *Expert Opin. Ther. Targets*, 2004, pp. 401-408, vol. 8, No. 5.

Puntambekar, P. et al. "Essential Role of Rac1/NADPH oxidase in nerve growth factor induction of TRPV1 expression" *Journal of Neurochemistry*, 2005, pp. 1689-1703, vol. 95.

(56) References Cited

OTHER PUBLICATIONS

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.
Qiu, S. et al. "Increasing Muscle Mass Improves Vascular Function in Obese (db/db) Mice" *Journal of the American Heart Association*, Jun. 25, 2014, pp. 1-18.
Rachmilewitz, D. et al. "Sulphydryl blocker induced small intestinal inflammation in rats: a new model mimicking Crohn's disease" *Gut*, 1997, pp. 358-365, vol. 41.
Rao, P. V. et al. "Expression of nonphagocytic NADPH oxidase system in the ocular lens" *Molecular Vision*, 2004, pp. 112-121, vol. 10.
Ray, R. et al. "NADPH oxidase and endothelial cell function" *Clinical Science*, 2005, pp. 217-226, vol. 109.
Reis, J. et al. "A closer look into NADPH oxidase inhibitors: Validation and insight into their mechanism of action" *Redox Biology*, 2020, pp. 1-13, vol. 32.
Reutens, A. T. et al. "A physician-initiated double-blind, randomised, placebo-controlled, Phase 2 study evaluating the efficacy and safety of inhibition of NADPH Oxidase with the first-in-class Nox-1/4 inhibitor, GKT137831, in adults with type 1 diabetes and persistently elevated urinary albumin excretion: Protocol and statistical considerations" *Contemporary Clinical Trials*, 2019, pp. 1-18.
Rios, F. J. et al. "Cholesteryl Ester-Transfer Protein Inhibitors Stimulate Aldosterone Biosynthesis in Adipocytes through Nox-Dependent Processes" *Journal of Pharmacology and Experimental Therapeutics*, Apr. 2015, pp. 27-34, vol. 353.
Rios, F. J. et al. "Off-Target Vascular Effects of Cholesteryl Ester Transfer Protein Inhibitors Involve Redox-Sensitive and Signal Transducer and Activator of Transcription 3-Dependent Pathways" *Journal of Pharmacology and Experimental Therapeutics*, May 2016, pp. 415-422, vol. 357.
Ritsick, D. R. et al. "Spring brings breezes, wheezes, and pollen oxidases" *The Journal of Clinical Investigation*, Aug. 2005, pp. 2067-2069, vol. 115, No. 8.
Rousset, F. et al. "IL-1 beta mediates MMP secretion and IL-1beta neosynthesis via upregulation of $p22^{phox}$ and NOX4 activity in human articular chondrocytes" *Osteoarthritis and Cartilage*, 2015, pp. 1972-1980, vol. 23.
Sampson, N. et al. "Inhibition of Nox4-dependent ROS signaling attenuates prostate fibroblast activation and abrogates stromal-mediated protumorigenic interactions" *International Journal of Cancer*, 2018, pp. 383-395, vol. 143.
Sasaki, H. et al. "Receptor activator of nuclear factor-κB ligand-induced mouse osteoclast differentiation is associated with switching between NADPH oxidase homologues" *Free Radical Biology & Medicine*, 2009, pp. 189-199, vol. 47.
Sasaki, H. et al. "NADPH oxidase-derived reactive oxygen species are essential for differentiation of a mouse macrophage cell line (RAW264.7) into osteoclasts" *J. Med. Invest.*, Feb. 2009, pp. 33-41, vol. 56.
Sato, K. et al. "In vivo lipid-derived free radical formation by NADPH oxidase in acute lung injury induced by lipopolysaccharide: a model for ARDS" *FASEB J.*, 2002, pp. 1713-1720, vol. 16.
Satoh, M. et al. "NAD(P)H oxidase and uncoupled nitric oxide synthase are major sources of glomerular superoxide in rats with experimental diabetic nephropathy" *Am. J. Physiol Renal Physiol*, 2005, pp. F1144-F1152, vol. 288.
Saxena, U. et al. "New approaches for treatment of diabetic nephropathy: the endothelium as a target for drug discovery" *Expert Opinion Ther. Targets*, 2001, pp. 539-545, vol. 5, No. 5.
Schildknecht, S. et al. "The NOX1/4 Inhibitor GKT136901 as Selective and Direct Scavenger of Peroxynitrite" *Current Medicinal Chemistry*, 2013, pp. 1-12, vol. 20, No. 1.
Sedeek, M. et al. "Renoprotective effects of a novel Nox1/4 inhibitor in a mouse model of Type 2 diabetes" *Clinical Science*, 2013, pp. 191-202, vol. 124.
Sedeek, M. et al. "Critical role of Nox4-based NADPH oxidase in glucose-induced oxidative stress in the kidney: implications in type 2 diabetic nephropathy" *Am. J. Physiol. Renal Physiol.*, 2010, pp. F1348-F1358, vol. 229.
Sharma, K. et al. "TGF-β impairs renal autoregulation via generation of ROS" *Am. J. Physiol Renal Physiol*, 2005, pp. F1069-F1079, vol. 288.
Shi, Y. et al. "Increased NAD(P)H Oxidase and Reactive Oxygen Species in Coronary Arteries After Balloon Injury" *Arterioscler Thromb Vasc Biol.*, 2001, pp. 739-745, vol. 21.
Shi, Q. et al. "Nox4 is a Target for Tuberin Deficiency Syndrome" *Scientific Reports*, Feb. 2018, pp. 1-14, vol. 8.
Silvestris, F. et al. "Cell Fusion and Hyperactive Osteoclastogenesis in Multiple Myeloma" *Adv Exp Med Biol.*, 2011, pp. 113-128, vol. 714.
Singh, N. et al. "Advances in the treatment of Parkinson's disease" *Progress in Neurobiology*, 2007, pp. 29-44, vol. 81.
Sirker, A. et al. "Involvement of NADPH Oxidases in Cardiac Remodelling and Heart Failure" *Am. J. Nephrol*, 2007, pp. 649-660, vol. 27.
Slade, R. et al. CAS:144:412361, 2006, Accession No. 2006:361235, pp. 1-4.
Somanna, N. K. et al. "The Nox1/4 Dual Inhibitor GKT137831 or Nox4 Knockdown Inhibits Angiotensin-II-Induced Adult Mouse Cardiac Fibroblast Proliferation and Migration. AT1 Physically Associates With Nox4" *Journal of Cellular Physiology*, 2016, pp. 1130-1141, vol. 231.
Sonta, T. et al. "Evidence for Contribution of Vascular NAD(P)H Oxidase to Increased Oxidative Stress in Animal Models of Diabetes and Obesity" *Free Radical Biology & Medicine*, 2004, pp. 115-123, vol. 37, No. 1.
STN on the Web, File Registry, RN=727370-48-1 (Aug. 16, 2004), 890865-63-1 (Jul. 6, 2006), p. 1.
STN on the Web, File Registry, RN=1040710-09-5, 1040708-33-5, 1040708-03-9, 1040703-20-5, 1040701-29-8. 1040699-70-4, 1040693-37-5, 1040691-81-3 (registered on Aug. 13, 2008); 1029773-59-8 (registered on Jun. 22, 2008); 1013978-57-8 (registered on Apr. 13, 2008); 1010935-30-4, 1010935-27-9, 1010915-05-5, 1010896-75-9, 1010892-94-0, 1010886-89-1, 1010882-92-4, 1010878-48-4, 1010876-16-0 (registered on Mar. 30, 2008); 1006654-90-5, 1006498-67-4 (registered on Mar. 4, 2008); 956282-84-1 (registered on Nov. 29, 2007); 890865-63-1 (registered on Jul. 6, 2006); 727370-48-1 (registered on Aug. 16, 2004); 669753-62-2 (registered on Apr. 1, 2004). pp. 1-3.
STN on the Web, File Registry, RN=895991-35-2 (Jul. 25, 2006), 895991-30-7 (Jul. 25, 2006), 895991-25-0 (Jul. 25, 2006), 895991-20-5 (Jul. 25, 2006), 895991-15-8 (Jul. 25, 2006),895991-02-3 (Jul. 25, 2006), 895990-97-3 (Jul. 25, 2006), 895990-92-8 (Jul. 25, 2006), 895990-73-5 (Jul. 25, 2006), 895990-68-8 (Jul. 25, 2006), 895990-54-2 (Jul. 25, 2006), 895990-49-5 (Jul. 25, 2006), 895990-40-6 (Jul. 25, 2006), 890865-63-1 (Jul. 6, 2006), 885906-56-9 (May 29, 2006), 885906-51-4 (May 29, 2006), 885906-35-4 (May 29, 2006), 885906-31-0 (May 29, 2006), 885906-27-4 (May 29, 2006), 885906-21-8 (May 29, 2006), 885890-49-3 (May 29, 2006), 885888-49-3 (May 29, 2006),847586-98-5 (Mar. 30, 2005),847586-96-3 (Mar. 30, 2005),847586-86-1 (Mar. 30, 2005),847586-83-8 (Mar. 30, 2005),847586-82-7 (Mar. 30, 2005),847586-81-6 (Mar. 30, 2005),847586-74-7 (Mar. 30, 2005),847586-72-5 (Mar. 30, 2005),847586-69-0 (Mar. 30, 2005),847586-56-5 (Mar. 30, 2005),847586-51-0 (Mar. 30, 2005),847586-49-6 (Mar. 30, 2005),847586-42-9 (Mar. 30, 2005),847586-38-3 (Mar. 30, 2005),847586-37-2 (Mar. 30, 2005),847586-36-1 (Mar. 30, 2005), pp. 1-20.
STN on the Web, File Registry, RN=914071-42-4 (Nov. 28, 2006), 909372-43-6 (Oct. 3, 2006), 908551-37-1 (Sep. 26, 2006), 906780-88-9 (Sep. 15, 2006), 906212-76-8 (Sep. 10, 2006), 906212-74-6 (Sep. 10, 2006), 906212-70-2 (Sep. 10, 2006), 906212-05-3 (Sep. 10, 2006), 899030-77-4 (Aug. 6, 2006), 899030-70-7 (Aug. 6, 2006), 899030-63-8 (Aug. 6, 2006), 899030-57-0 (Aug. 6, 2006), 899026-88-1 (Aug. 6, 2006), 899026-83-6 (Aug. 6, 2006), 899026-78-9 (Aug. 6, 2006), 899026-67-6 (Aug. 6, 2006), 899026-57-4 (Aug. 6, 2006), 899026-52-9 (Aug. 6, 2006), 899026-47-2 (Aug. 6, 2006), 899026-42-7 (Aug. 6, 2006), 899026-37-0 (Aug. 6, 2006),

(56) References Cited

OTHER PUBLICATIONS 899026-32-5 (Aug. 6, 2006), 899026-19-8 (Aug. 6, 2006), 897547-95-4 (Jul. 31, 2006), 897547-93-2 (Jul. 31, 2006), 897547-92-1 (Jul. 31, 2006), 897547-91-0 (Jul. 31, 2006), 897547,90-9 (Jul. 31, 2006), 896654-25-4 (Jul. 28, 2006), 896654-23-2 (Jul. 28, 2006), 896654-21-0 (Jul. 28, 2006), 896654-19-6 (Jul. 28, 2006), 896056-52-3 (Jul. 25, 2006), 896056-49-8 (Jul. 25, 2006), 896056-46-5 (Jul. 25, 2006), 895991-49-8 (Jul. 25, 2006), 895991-44-3 (Jul. 25, 2006), 895991-40-9 (Jul. 25, 2006), pp. 1-18.
STN on the Web, File Registry, RN=847586-32-7 (Mar. 30, 2005), 847586-30-5 (Mar. 30, 2005), 847586-24-7 (Mar. 30, 2005), 847586-23-6 (Mar. 30, 2005),847573-56-2 (Mar. 30, 2005), 847573-45-9 (Mar. 30, 2005),847573-43-7 (Mar. 30, 2005),847573-41-5 (Mar. 30, 2005), 847573-40-4 (Mar. 30, 2005), 847573-35-7 (Mar. 30, 2005),847573-31-3 (Mar. 30, 2005), 847573-25-5 (Mar. 30, 2005),847573-23-3 (Mar. 30, 2005),847573-13-1 (Mar. 30, 2005),847573-07-3 (Mar. 30, 2005),847572-88-7 (Mar. 30, 2005), 847572-77-4 (Mar. 30, 2005), 847572-75-2 (Mar. 30, 2005), 847572-66-1 (Mar. 30, 2005), 847572-61-6 (Mar. 30, 2005), 847572-60-5 (Mar. 30, 2005),847572-57-0 (Mar. 30, 2005), 847572-51-4 (Mar. 30, 2005),847572-38-7 (Mar. 30, 2005),847572-35-4 (Mar. 30, 2005),847572-33-2 (Mar. 30, 2005), 727370-48-1 (Aug. 16, 2004),669753-72-4 (Apr. 1, 2004), 669753-67-7 (Apr. 1, 2004), 669753-62-2 (April 1, 204), 516455-29-1 (May 16, 2003), pp. 1-16.
Sturrock, A. et al. "Transforming growth factor-β1 induces Nox4 NAD(P)H oxidase and reactive oxygen species-dependent proliferation in human pulmonary artery smooth muscle cells" *Am J Physiol Lung Cell Mol Physiol*, 2006, pp. L661-L673, vol. 290.
Sturrock, A. et al. "Nox4 mediates TGF-β1-induced retinoblastoma protein phosphorylation, proliferaton, and hypertrophy in human airway smooth muscle cells" *Am. J Physiol. Lung. Cell Mol. Physiol.*, 2007, pp. L1543-L1555. vol. 292, No. 6.
Sun, Q. et al. "Pharmacological inhibition of NOX4 ameliorates alcohol-induced liver injury in mice through improving oxidative stress and mitochondrial function" *Biochimica et Biophysica Acta*, 2017, pp. 2912-2921, vol. 1861.
Takac, I. et al. "The E-loop Is Involved in Hydrogen Peroxide Formation by the NADPH Oxidase Nox4" *J. Biol. Chem.*, Apr. 15, 2011, pp. 13304-13313, vol. 286, No. 15.
Tang, X. N. et al. "Apocynin Improves Outcome in Experimental Stroke with a Narrow Dose Range" *Neuroscience*, 2008, pp. 556-562, vol. 154.
Tang, C. T. et al. "NOX4, a new genetic target for anti-cancer therapy in digestive system cancer" *Journal of Digestive Diseases*, 2018, pp. 578-585, vol. 19.
Thabut, G. et al. "Tumor Necrosis Factor-α Increases Airway Smooth Muscle Oxidants Production through a NADPH Oxidase-like System to Enhance Myosin Light Chain Phosphorylation and Contractility" *The Journal of Biological Chemistry*, Jun. 21, 2002, pp. 22814-22821, vol. 277, No. 25.
Tojo, A. et al. "Suppressing renal NADPH oxidase to treat diabetic nephropathy" *Expert Opin. Ther. Targets*, 2007, pp. 1011-1018, vol. 11, No. 8.
Ushio-Fukai, M. et al. "Reactive oxygen species and angiogenesis: NADPH oxidase as target for cancer therapy" *Cancer Letters*, 2008, pp. 37-52, vol. 266.
Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.
Vendrov, A. E. et al. "NADPH Oxidases Regulate CD44 and Hyaluronic Acid Expression in Thrombin-treated Vascular Smooth Muscle Cells and in Atherosclerosis" *The Journal of Biological Chemistry*, Aug. 20, 2010, pp. 26545-26557, vol. 285, No. 34.
Vendrov, A. E. et al. "NOX4 NADPH Oxidase-Dependent Mitochondrial Oxidative Stress in Aging-Associated Cardiovascular Disease" *Antioxidants & Redox Signaling*, 2015, pp. 1-21.
Vernet, P. et al. "Analysis of Reactive Oxygen Species Generating Systems in Rat Epididymal and Spermatozoa" *Biology of Reproduction*, 2001, pp. 1102-1113, vol. 65.
Wang, W. et al. "Effect of the NADPH Oxidase Inhibitor Apocynin on Septic Lung Injury in Guinea Pigs" *American Journal of Respiratory and Critical Care Medicine*, 1994, pp. 1449-1452, vol. 150.
Wang, C. et al. "Ameliorative effect of berberine on endothelial dysfunction in diabetic rats induced by high-fat diet and streptozotocin" *European Journal of Pharmacology*, 2009, pp. 131-137, vol. 620.
Wang, Z. et al. "Osteoclasts and odontoclasts: signaling pathways to development and disease" *Oral Diseases*, 2011, pp. 129-142, vol. 17.
Wang, J. et al. "Nox2 and Nox4 Participate in ROS-Induced Neuronal Apoptosis and Brain Injury During Ischemia-Reperfusion in Rats" *Acta Neurochirurgica*, 2020, pp. 47-54, Supplement 127.
Waning, D. L. et al. "Excess TGF-β mediates muscle weakness associated with bone metastases in mice" *Nature Medicine*, 2015, pp. 1-14, Online Methods pp. 1-4.
Wegner, A. M. et al. "Acute Changes in NADPH Oxidase 4 in Early Post-Traumatic Osteoarthritis" *J Orthop Res*, 2019, pp. 2429-2436, vol. 37.
Wilkinson-Berka, J. et al. "NADPH Oxidase, NOX1, Mediates Vascular Injury in Ischemic Retinopathy" *Antioxidants & Redox Signaling*, 2013, pp. 1-15.
Wolff, M. E. et al. "Burger's Medicinal Chemistry and Drug Discovery", 1994 Wiley-Interscience, Fifth Edition, vol. I: Principles and Practice, pp. 975-977.
Written Opinion in International Application No. PCT/IB2011/050667, Jun. 22, 2011, pp. 1-8.
Written Opinion in International Application No. PCT/IB2011/050668, Jul. 11, 2011, pp. 1-9.
Written Opinion in International Application No. PCT/IB2010/054329, Mar. 1, 2011, pp. 1-8.
Written Opinion in International Application No. PCT/IB2012/056286, Jan. 22, 2013, pp. 1-10.
Written Opinion in International Application No. PCT/EP2008/053390, Jul. 21, 2008, pp. 1-6.
Written Opinion in International Application No. PCT/IB2009/054148, Oct. 12, 2009, pp. 1-8.
Written Opinion in International Application No. PCT/IB2009/054150, Oct. 13, 2010, pp. 1-11.
Written Opinion in International Application No. PCT/IB2009/054155, Nov. 6, 2010, pp. 1-7.
Written Opinion in International Application No. PCT/IB2009/054156, Mar. 3, 2010, pp. 1-10.
Written Opinion in International Application No. PCT/EP2008/053704, Jul. 7, 2008, pp. 1-7.
Wu, D. et al. "NADPH oxidase mediates oxidative stress in the 1-methyl-4-phenyl-1,2,3,6-tetrahydropyridine model of Parkinson's disease" *PNAS*, May 13, 2003, pp. 6145-6150, vol. 100, No. 10.
Wu, D.-C. et al. "The inflammatory NADPh oxidase enzyme modulates motor neuron degeneration in amyotrophic lateral sclerosis mice" *PNAS*, Aug. 8, 2006, pp. 12132-12137, vol. 103, No. 32.
Yang, S. et al. "Characterization of Interferon Gamma Receptors on Osteoclasts: Effect of Interferon Gamma on Osteoclastic Superoxide Generation" *Journal of Cellular Biochemistry*, 2002, pp. 645-654, vol. 84.
Yang, S. et al. "Nox4 Participates in Superoxide Production During Osteoclast Differentiation and Bone Resorption" *Journal of Bone and Mineral Research*, Oct. 1, 2004, p. SA314, vol. 19, abstract only.
Yang, S. et al. "A New Superoxide-generating Oxidase in Murine Osteoclasts" *The Journal of Biological Chemistry*, Feb. 23, 2001, pp. 5452-5458, vol. 276, No. 8.
Yang, S. et al. "Expression of Nox4 in Osteoclasts" *Journal of Cellular Biochemistry*, 2004, pp. 238-248, vol. 92.
Yauger, Y. J. et al. "Iron accentuated reactive oxygen species release by NADPH oxidase in activated microglia contributes to oxidative stress in vitro" *Journal of Neuroinflammation*, 2019, pp. 1-15, vol. 16, No. 41.
Yoshikawa, Y. et al. "Nox4 Promotes Neural Stem/Precursor Cell Proliferation and Neurogenesis in the Hippocampus and Restores Memory Function Following Trimethyltin-Induced Injury" *Neuroscience*, 2019, pp. 193-205, vol. 398.

(56) References Cited

OTHER PUBLICATIONS

You, Y.-H. et al. "Metabolomics Reveals a Key Role for Fumarate in Mediating the Effects of NADPH Oxidase 4 in Diabetic Kidney Disease" *Journal of the American Society of Nephrology*, 2015, pp. 1-16, vol. 27.

Yu, L. et al. "Megakaryocytic Leukemia 1 Bridges Epigenetic Activation of NADPH Oxidase in Macrophages to Cardiac Ischemia-Reperfusion Injury" *Circulation*, Dec. 11, 2018, pp. 2820-2836, vol. 138.

Zanetti, F. et al. "Nicotine mediates oxidative stress and apoptosis through cross talk between NOX1 and Bcl-2 in lung epithelial cells" *Free Radical Biology and Medicine*, 2014, pp. 173-184, vol. 76.

Zeng, C. et al. "NOX4 supports glycolysis and promotes glutamine metabolism in non-small cell lung cancer cells" *Free Radical Biology and Medicine*, 2016, pp. 236-248, vol. 101.

Zeng, S. et al. "Nox1/4 dual inhibitor GKT137831 attenuates hypertensive cardiac remodelling associating with the inhibition of ADAM17-dependent proinflammatory cytokines-induced signalling pathways in the rats with abdominal artery constriction" *Biomedicine & Pharmacotherapy*, 2019, pp. 1907-1914, vol. 109.

Zhang, J. et al. "Tumoral NOX4 recruits M2 tumor-associated macrophages via ROS/PI3K signaling-dependent various cytokine production to promote NSCLC growth" *Redox Biology*, 2019, pp. 1-14, vol. 22.

Zhao, W. et al. "Kidney Fibrosis in Hypertensive Rats: Role of Oxidative Stress" *Am J Nephrol*, 2008, pp. 548-554, vol. 28.

Zhao, W. et al. "Danshenol A inhibits TNF-α-induced expression of intercellular adhesion molecule-1 (ICAM-1) mediated by NOX4 in endothelial cells" *Scientific Reports*, 2017, pp. 1-13, vol. 7.

Zhao, W. et al. "Aqueous extract of *Salvia miltiorrhiza* Bunge-Radix *Puerariae* herb pair ameliorates diabetic vascular injury by inhibiting oxidative stress in streptozotocin-induced diabetic rats" *Food and Chemical Toxicology*, 2019, pp. 97-107, vol. 129.

Zhao, W. et al. "Tert-butyl hydroperoxide (t-BHP) induced apoptosis and necroptosis in endothelial cells: Roles of NOX4 and mitochondrion" *Redox Biology*, 2017, pp. 524-534, vol. 11.

Zhao, Q. D. et al. "NAPDH Oxidase 4 Induces Cardiac Fibrosis and Hypertrophy Through Activating Akt/mTOR and NFκB Signaling Pathways" *Circulation*, Feb. 17, 2015, pp. 643-655, vol. 131, Online Supplemental Data pp. 1-25.

Andrews, M. C. et al. "Immunotherapy resistance: the answers lie ahead—not in front—of us" *Journal for Immuno Therapy of Cancer*, 2017, pp. 1-3, vol. 5, No. 10.

Balar, A. V. et al. "PD-1 and PD-L1 antibodies in cancer: current status and future directions" *Cancer Immunol Immunother.*, Feb. 17, 2017, pp. 551-564, vol. 66, No. 5.

Bartlett, D. L. et al. "Oncolytic viruses as therapeutic cancer vaccines" *Molecular Cancer*, 2013, pp. 1-16, vol. 12, No. 103.

Block, K. et al. "Aiding and abetting roles of NOX oxidases in cellular transformation" *Nat Rev Cancer.*, Sep. 2012, pp. 1-24, vol. 12, No. 9.

Brentjens, R. et al. "CD19-targeted T cells rapidly induce molecular remissions in adults with chemotherapy-refractory acute lymphoblastic leukemia" *Sci Transl Med.*, Mar. 20, 2013, pp. 1-19, vol. 5, No. 177.

Chen, C. et al. "The Role of NOX4 and TRX2 in Angiogenesis and Their Potential Cross-Talk" *Antioxidants*, 2017, pp. 1-15, vol. 6, No. 2.

Ford, K. et al. "NOX4 Inhibition Potentiates Immunotherapy by Overcoming Cancer-Associated Fibroblast-Mediated CD8 T-cell Exclusion from Tumors" *Cancer Research*, 2020 pp. OF1-OF15.

Fukuhara, H. et al. "Oncolytic virus therapy: A new era of cancer treatment at dawn" *Cancer Science*, Oct. 2016, pp. 1373-1379, vol. 107, No. 10.

Gaggini, F. et al. "Design, synthesis and biological activity of original pyrazolo-pyrido-diazepine, -pyrazine and -oxazine dione derivatives as novel dual Nox4/Nox1 inhibitors" *Bioorganic & Medicinal Chemistry*, 2011, pp. 6989-6999, vol. 19.

Gardner, V. et al. "Anti-VEGF Therapy in Cancer: A Double-Edged Sword" *Physiologic and Pathologic Angiogenesis—Signaling Mechanisms and Targeted Therapy*, Chapter 19, 2017, pp. 385-410.

Grupp, S. A. et al. "Chimeric Antigen Receptor-Modified T Cells for Acute Lymphoid Leukemia" *N Engl J Med.*, Apr. 18, 2013, pp. 1-16, vol. 368, No. 16.

Hanley, C. J. et al. "Targeting the Myofibroblastic Cancer-Associated Fibroblast Phenotype Through Inhibition of NOX4" *J Natl Cancer Inst*, 2018, pp. 109-120, vol. 110, No. 1.

Huang, C. et al. "Small interfering RNA therapy in cancer: mechanism, potential targets, and clinical applications" *Expert Opinion on Therapeutic Targets*, 2008, pp. 637-645, vol. 12, No. 5.

Iwai, Y. et al. "Cancer immunotherapies targeting the PD-1 signaling pathway" *Journal of Biomedical Science*, 2017, pp. 1-11, vol. 24, No. 26.

June, C. H. et al. "CAR T cell immunotherapy for human cancer" *Science*, Mar. 23, 2018, pp. 1-5, vol. 359.

Kochenderfer, J. N. et al. "Eradication of B-lineage cells and regression of lymphoma in a patient treated with autologous T cells genetically engineered to recognize CD19" *Blood*, Nov. 18, 2010, pp. 4099-4102, vol. 116, No. 20.

Martin, S. E. et al. "Applications of RNA Interference in Mammalian Systems" *Annu. Rev. Genomics Hum. Genet.*, 2007, pp. 81-108 (Contents p. v-vi), vol. 8.

Mishra, A. "PD-1/PD-L1 biology and immunotherapy in HPV-positive oral cancers" *Future Oncol.*, 2017, pp. 1907-1909, vol. 13, No. 22.

Porter, D. L. et al. "Chimeric Antigen Receptor-Modified T Cells in Chronic Lymphoid Leukemia" *N Engl J Med.*, Aug. 25, 2011, pp. 1-12, vol. 365, No. 8.

Ribas, A. et al. "Association of Pembrolizumab With Tumor Response and Survival Among Patients With Advanced Melanoma" *JAMA*, Apr. 19, 2016, pp. 1600-1609, vol. 315, No. 15.

Rice, J. et al. "Critical Components of a DNA Fusion Vaccine Able to Induce Protective Cytotoxic T Cells Against a Single Epitope of a Tumor Antigen" *The Journal of Immunology*, 2002, pp. 3908-3913, vol. 169.

Rice, J. et al. "DNA vaccines: precision tools for activating effective immunity against cancer" *Nat Rev Cancer*, Feb. 2008, pp. 108-120, vol. 8.

Sharma, P. et al. "Immune Checkpoint Targeting in Cancer Therapy: Towards Combination Strategies with Curative Potential" *Cell*, Apr. 9, 2015, pp. 1-19, vol. 161, No. 2.

Soto Chervin, C. et al. "Current clinical immunotherapeutic approaches for head and neck cancer" *F1000Research*, May 5, 2016, pp. 1-8.

Stalin, J. et al. "Inhibition of host NOX1 blocks tumor growth and enhances checkpoint inhibitor-based immunotherapy" *Life Science Alliance*, 2019, pp. 1-16, vol. 2, No. 4, e201800265.

Teixeira, G. et al. "Therapeutic potential of NADPH oxidase 1/4 inhibitors" *British Journal of Pharmacology*, 2017, pp. 1647-1669, vol. 174.

Topalian, S. L. et al. "Cancer Immunotherapy Comes of Age" *Journal of Clinical Oncology*, Dec. 20, 2011, pp. 4828-4836, vol. 29, No. 36.

Yaddanapudi, K. et al. "Cancer vaccines, Looking to the future" *OncoImmunology*, Mar. 2013, pp. e23403-1-e23403-7, vol. 2, Issue. 3.

Written Opinion in International Application No. PCT/EP2018/079945, Feb. 20, 2019, pp. 1-10.

Ferris, R. L. "Immunology and Immunotherapy of Head and Neck Cancer" *Journal of Clinical Oncology*, Oct. 10, 2015, pp. 3293-3304, vol. 33, No. 29.

Economopoulou, P. et al. "The promise of immunotherapy in head and neck squamous cell carcinoma: combinatorial immunotherapy approaches" *ESMO Open*, 2017, pp. 1-9, vol. 1, e000122.

Lombardi, M. Y. et al. "Glioblastoma Genomics: A Very Complicated Story" in Glioblastoma, edited by Steven De Vleeschouwer, Sep. 2017, pp. 1-41, Codon Publications, Brisbane, Australia.

Demidenko, E. et al. "Statistical determination of synergy based on Bliss definition of drugs independence" PLoS ONE, Nov. 25, 2019, pp. 1-22, vol. 14, No. 11, e0224137.

Ilson, D. H. "Esophageal Cancer Chemotherapy: Recent Advances" *Gastrointestinal Cancer Research*, Mar./Apr. 2008, pp. 85-92, vol. 2, Issue 2.

\* cited by examiner

USE OF NOX INHIBITORS FOR TREATMENT OF CANCER

CROSS-REFERENCE TO RELATED APPLICATION

This application is the U.S. national stage application of International Patent Application No. PCT/EP2018/079945, filed Nov. 1, 2018, which claims priority of European Patent Application No. 17199601.0, filed Nov. 1, 2017.

FIELD OF THE INVENTION

The present invention relates to the use of NADPH oxidase (NOX) inhibitors, in particular NOX4 or NOX4/1 dual or NOX1 inhibitors, for the treatment of solid cancers in combination with a cancer immunotherapy or an anti-VEGF treatment and related combined formulations and regimen.

BACKGROUND OF THE INVENTION

Cancer cells face multiple cellular stresses such as hypoxia, increased metabolic demand, genomic instability, immune surveillance, lack of nutriments, changing environment after metastasis and stresses resulting to treatments such as radiotherapy, chemotherapies and targeted therapies.

NADPH oxidases (NOX) are a family of enzymes harbouring 6 trans-membrane domain and that transfer electrons across biological membranes. Those enzymes are dedicated reactive oxygen species-generating enzymes that broadly and specifically regulate redox-sensitive signaling pathways that are involved in cancer development and progression and act at specific cellular membranes and microdomains through the activation of oncogenes and the inactivation of tumour suppressor proteins. NOX enzymes are considered to be an essential part of adaptive stress response, in particular for cancer cells, thereby allowing those cells to adapt and survive (Block et al., 2012, *Nature Reviews*, 627-637).

Marked induction of NOX expression has been reported in cancer cells and in host cells within the tumor environment.

The interplay between tumor microenvironment and cancer cells is recognized to have a major role for tumor growth and metastasis. Cancer-associated-fibroblasts (CAFs) are the most abundant cells found in the tumour stroma. CAFs, and their fibroblast-to-myofibroblast transdifferentiation lead to tumor growth and generally correlate with poor prognosis in multiple cancer types. While CAF promote "many of the hallmarks of malignancy", recent studies have highlighted a role in promoting tumor immune evasion with CAF-rich cancers which are designated as being "immune cold" for their poor therapeutic response to cancer immunotherapies such as immune checkpoint inhibitors and cancer vaccines and their propensity to evolve to metastasis.

Furthermore, high CAF content induces a dense stroma and dense tumor microenvironment which increases interstitial fluid pressure and thereby acts as a barrier to drug delivery, leading to poor accumulation of chemotherapies in tumours.

In particular, melanoma is known as an exceptionally aggressive and treatment-resistant human cancer. Although progresses have been made in the past decade, including the development of immunotherapy using immune checkpoint inhibitors, treatment for unresectable stage III, stage IV, and recurrent melanoma is still challenging with limited response rate, severe side effects and poor prognosis. Melanoma is not only driven by malignant melanocytes, but also by the altered communication between neoplastic cells and non-malignant cell populations, including fibroblasts, endothelial and inflammatory cells, in the tumor stroma. CAFs remodel the extracellular matrix (ECM) and architecture of the diseased tissue and secrete chemical factors, which all together promote the transformation process by encouraging tumor growth, angiogenesis, inflammation and metastasis and contribute to drug resistance. If it has been recently shown that NOX4 regulates myofibroblastic CAF differentiation in multiple cancers (Hanley et al., 2018, *J Natl Cancer Inst.*, 110), the origin of CAFs and precise mechanisms by which CAFs contribute to cancer progression and drug resistance still remain poorly understood. Further, Hanley et al., 2018 did not point towards any specific anti-cancer immunotherapeutic agent as adjunct treatment with NOX4 inhibition.

Immunotherapy continues to gain interest as an effective therapeutic strategy across several cancer types such as melanoma, non-small cell lung cancer, small cell lung cancer, head and neck cancer, renal cell cancer, bladder cancer, ovarian cancer, uterine endometrial cancer, uterine cervical cancer, uterine sarcoma, gastric cancer, esophageal cancer, colon cancer, hepatocellular carcinoma, breast cancer, Merkel cell carcinoma, thyroid cancer, Hodgkin lymphoma, follicular lymphoma, diffuse large B-cell lymphoma, mycosisfungoides, peripheral T-cell lymphoma, and include various approaches, ranging from stimulating effector mechanisms to counteracting inhibitory and suppressive mechanisms. Strategies to activate effector immune cells include vaccination with tumor antigens or augmentation of antigen presentations to increase the ability of the patient's own immune system to increase the efficacy of the immune response against neoplastic cells (Yaddnapudi et al., 2013, *Cancer vaccines, Oncoimmunology*, 2(3), e23403). Additional stimulatory strategies encompass adoptive cellular therapy (ACT), the administration of oncolytic viruses (OVs) for the initiation of systemic antitumor immunity, and the use of antibodies targeting members of the tumor necrosis factor receptor superfamily to enhance T cell activity. Strategies to neutralize immunosuppressor mechanisms include chemotherapy (cyclophosphamide), antibodies to diminish regulatory T cells (CD25-targeted antibodies), and antibodies against immune-checkpoint molecules such as CTLA-4, PD1 and PD-L1.

The field of cancer immunotherapy has been recently encouraged primarily by the approval of the autologous cellular immunotherapy, sipuleucel-T for the treatment of prostate cancer in 2010 (Topalian et al., 2011, *J. Clin. Oncol.*, 29: 4828-36) and the approval of the anti-cytotoxic T lymphocyte-associated protein 4 (CTLA-4) antibody, ipilimumab, and of anti-programmed cell death protein 1 (PD1) antibodies for the treatment of melanoma in 2011 and 2014 (Sharma et al., 2015, *Cell*, 161:205-14).

Successful anti-cancer effect has been demonstrated through the use of immune checkpoint blockade targeting cytotoxic T-lymphocyte associated protein 4 (CTLA-4) and programmed-death 1 (PD-1)/PD-1 ligand (PD-L1), with the highest objective response rates observed in cancer types with a high mutational burden such as melanoma and non-small cell lung cancer (Andrews et al., 2017, *Journal for ImmunoTherapy of Cancer*, 25:10). However significant limitations exist with these therapeutic agents with objective responses to PD-1 blockade observed in only 30-40% of patients and the majority of patients demonstrating innate resistance. Acquired resistance to anti-PD-1 therapy is also a problem, with approximately one quarter of responders later demonstrating disease progression (Ribas et al., 2016, *JAMA*, 315:1600-9).

Further, resistance of solid tumors to anti-cancer treatment has also been observed to antiangiogenic therapies and has become a high concern for the use of anti-VEGF therapies (Gardner et al., 2017, *Chapter 19, Anti-VEGF Therapy in Cancer: A Double-Edged Sword*, dx.doi.org/10.5772/66763, anti-PDGF agents) since despite their encouraging beneficial effects, patients inevitably develop resistance and frequently fail to demonstrate significantly better overall survival.

Therefore, in view of the recent developments of various strategies in cancer immunotherapy such as cancer vaccines, adoptive cellular immunotherapy, immune checkpoint blockade, and oncolytic viruses and antiangiogenic therapies but also the encountered limitations to their efficacy, there is a growing need of developing efficient anti-cancer therapies for solid tumor cancers, in particular for cancers prone for developing a resistance to immunotherapy or antiangiogenic therapies, which would allow restoring sensitivity to immunotherapy or antiangiogenic treatments or potentiate cancer vaccine treatments.

SUMMARY OF THE INVENTION

The present invention is directed towards the unexpected findings that the recently found ability of pharmacological inhibition of NOX4 to revert the myofibroblastic-CAF phenotype in different cancer cells lines and suppresses tumor growth in multiple CAF-rich tumor models (TC1+CAF [HNSCC model], 4T1+CAF [breast cancer], MMTV-PyVT (breast cancer), MMTV-Her2/neu (breast cancer) both in vitro and/or in vivo (Hanley et al., 2018, *J Natl Cancer Inst.*, 110) is useful for synergistically potentiating cancer immunotherapy or reversing anti-VEGF treatment elicited resistance.

The present invention is directed towards the unexpected findings that NOX4/1 dual inhibitors are able to restore sensitivity to immunotherapy and/or improve response to immunotherapy and to antiangiogenic therapies.

The present invention is directed to compositions and methods useful for the restoration of responsiveness to immunotherapy, in particular for the restoration of responsiveness to cancer vaccines such as HPV and immune checkpoint blockade such as with PD-1 inhibitors, PD-L1 inhibitors, and CTLA-4 inhibitors.

In particular, the present invention is directed towards the unexpected findings that NOX4 inhibitors are able to restore sensitivity to anti-tumour immunotherapy and/or improve response to immunotherapy.

In particular, the present invention is directed towards the unexpected findings that NOX1 inhibitors are able to improve response to antiangiogenic therapies.

The present invention is further directed to compositions and methods useful for the restoration of responsiveness to anti-angiogenic therapies, in particular for the restoration of responsiveness to an anti-VEGF treatment and/or the decrease or avoid the appearance of a resistance to an anti-VEGF treatment.

A first aspect of the invention provides a NOX4 inhibitor or a NOX4/1 dual or a NOX1 inhibitor for use in the treatment of solid tumor cancers presenting or susceptible to present a resistance to immunotherapy or to an anti-angiogenic agent, in particular to an anti-VEGF treatment, wherein said NOX4 (or NOX4/1 or NOX1) inhibitor is to be administered in combination with an anti-cancer immunotherapeutic agent or an anti-angiogenic agent.

Another aspect of the invention provides a use of one or more NOX4 or NOX4/1 dual or NOX1 inhibitors for the preparation of a pharmaceutical composition for the treatment of solid tumor cancers presenting or susceptible to present a resistance to immunotherapy or to an anti-angiogenic agent, in particular to an anti-VEGF treatment, wherein said one or more NOX4 or NOX4/1 or NOX1 inhibitor is to be administered in combination with an anti-cancer immunotherapeutic agent or an anti-angiogenic agent.

Another aspect of the invention relates to a pharmaceutical composition containing at least one NOX4 or NOX4/1 or NOX1 inhibitor according to the invention, as well as tautomers, geometrical isomers, optically active forms and pharmaceutically acceptable salts thereof combined with at least one anti-cancer immunotherapeutic agent or at least one further anti-angiogenic agent and at least one pharmaceutically acceptable carrier, diluent or excipient thereof.

Another aspect of the invention relates to a method for treating a subject suffering from a solid tumour cancer presenting or susceptible to present a resistance to immunotherapy or to an anti-angiogenic agent, in particular to an anti-VEGF treatment, said method comprising administering an effective amount of one or more NOX4 or NOX4/1 or NOX1 inhibitor, in combination with an anti-cancer immunotherapeutic agent or an anti-angiogenic agent in a subject in need thereof.

Another aspect of the invention relates to a method for restoring or increasing responsiveness to anti-cancer immunotherapy, in particular restoring sensitivity to immunotherapeutic treatment, notably turning cold tumours towards a hot state, in a subject, said method comprising administering an effective amount of one or more NOX4 or NOX4/1 or NOX1 inhibitor or a pharmaceutical formulation thereof in combination with an anti-cancer immunotherapeutic agent in a subject in need thereof.

Another aspect of the invention relates to a method for restoring or increasing responsiveness to anti-cancer anti-angiogenesis, in particular restoring sensitivity to anti-VEGF treatment or preventing resistance to anti-VEGF treatment in a subject, said method comprising administering an effective amount of one or more NOX4 or NOX4/1 or NOX1 inhibitor or a pharmaceutical formulation thereof in combination with an anti-angiogenic agent in a subject in need thereof.

Other features and advantages of the invention will be apparent from the following detailed description.

DETAILED DESCRIPTION OF THE INVENTION

Figure 1A:
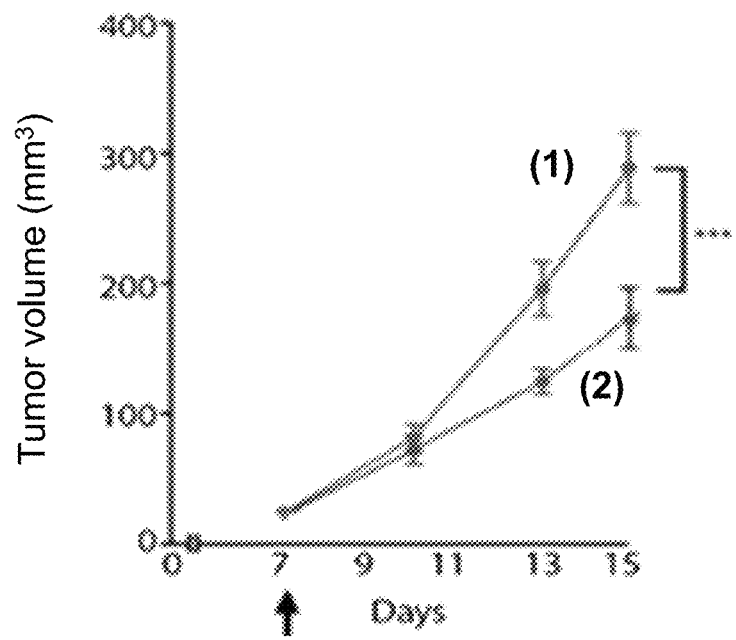
FIG. 1 shows the effects of a treatment with a NOX4 inhibitor (GKT) on the relocation of the DCD8+ T cells into tumors 4T1 when cancer cells were co-injected with cancer-associated fibroblasts (CAF) orthotopically into the mammary fat pad as described in Example 1. A: tumor volume increase expressed in $mm^3$ versus days after the injection (arrow) of either the combination of the tumor cells with CAFs and vehicle (1) or the combination of the tumor cells with CAFs and NOX4 inhibitor (2); B: Immunochemistry and quantification thereof showing the efficacy of the treatment with the NOX4 inhibitor in reducing SMA-positive CAF in tumours; C: Immunochemistry (and quantification thereof) showing that treatment with the NOX4 inhibitor results in relocation of CD8+ T-cells from the tumour edge into the centre of the tumour.

The expression "NOX inhibitor" as used herein refers to any substances that are able to totally or partially inhibit, block, attenuate, or interfere with NOX4 and/or NOX1. The term directly is defined as that the compound affects the enzymatic activity of the enzyme, the cellular localization, the stability of the protein, the expression of the messenger RNA or the protein. Preferably, a NOX4/NOX1 inhibitor should be able to diminish enzyme activity and ROS production in a cell free assay using membrane expressing only the NOX isoform NOX4/1 protein, such as recombinant protein NOX4/1. Thus, the term "inhibitors" is intended to include but is not limited to, molecules, which inhibit completely or partially the activity of NADPH oxidase 4 and/or NADPH oxidase 1. According to a particular embodiment, NOX4/1 inhibitors have a major NOX inhibitory activity component towards NOX4 and/or NOX1 compared to other NOX proteins, for example to NOX2 and/or NOX3/5. According to a particular embodiment, NOX4/1 inhibitors have a major NOX inhibitory activity on NOX4/1 about at least five times higher than on other NOX proteins.

For example, NOX4/1 inhibitors include small molecules, peptides, peptidomimetics, chimeric proteins, natural or unnatural proteins, nucleic acid derived polymers (such as DNA and RNA aptamers, siRNAs, shRNAs, PNAs, or LNAs), fusion proteins with NOX4/1 antagonizing activities, antibody antagonists such as neutralizing anti-NOX4/1 antibodies, or gene therapy vectors driving the expression of such NOX4/1 antagonists.

In particular, NOX4/1 inhibitors are agents that present an inhibitory constant Ki of less than 5 micromolar in a functional ROS production assay such as those described in Gaggini et al., 2011, *Bioorganic and Medicinal chemistry*, Vol. 19(23), 6989-6999. For example, NOX4/1 inhibitors are agents that inhibit ROS production in a range of about less than 1 microM, such as between about 30 to 300 nanomolar in a cell free assay using membrane expressing only the NOX isoform NOX4 or NOX1 protein, such as recombinant protein NOX4 or NOX1.

The term "siRNA" refers to small interfering RNA, which are double stranded RNA (about 19-23 nucleotides) able to knock down or silence a targeted mRNA from a target gene. Artificial siRNAs can be either chemically synthesized as oligonucleotides or cloned into a plasmid or a virus vector (adenovirus, retrovirus or lentivirus) as short hairpin RNAs to generate a transient or stable transfection in any type of cells (Martin et al., 2007, *Ann. Rev. Genomics Hum. Genet.*, 8:81-108; Huang et al., 2008, *Expert. Opin. Ther. Targets*, 12(5), 637-645).

The expression "solid tumour cancer" includes, glioblastoma, lung cancer (small cell and non-small cell), breast cancer, ovarian cancer, cervical cancer, uterus cancer, head and neck cancer, melanoma, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer, in particular glioblastoma.

As used herein, "treatment" and "treating" and the like generally mean obtaining a desired pharmacological and physiological effect. The term "treatment" as used herein covers any treatment of a disease in a mammal, particularly a human, and includes inhibiting the disease, i.e., arresting its development; or relieving the disease, i.e. causing regression of the disease and/or its symptoms or conditions such as tumor growth arrest or tumor regression.

The term "subject" as used herein refers to mammals. For examples, mammals contemplated by the present invention include human, primates, domesticated animals such as cattle, sheep, pigs, horses, laboratory rodents, dogs and the like.

The term "effective amount" as used herein refers to an amount of at least one particle or a pharmaceutical formulation thereof according to the invention that elicits the biological or medicinal response in a tissue, system, animal, or human that is being sought. In one embodiment, the effective amount is a "therapeutically effective amount" for the alleviation of the symptoms of the disease or condition being treated. Typically, an effective amount can be used to inhibit the growth of cancer cells, i.e. any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, defer the growth, reduce the aggressiveness, or prevent or inhibit metastasis of a cancer in a patient. Those skilled in the art can readily determine, by any of a variety of suitable indicia, whether cancer cell growth is inhibited.

The term "efficacy" of a treatment according to the invention can be measured based on changes in the course of a disease in response to a use or a method according to the invention. The efficacy of a treatment of a cancer according to the invention can be measured by a reduction of tumour volume, and/or an increase of progression free survival time and/or increased health and well-being of the subject (e.g.

repressing a cancer). Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced using well known imaging methods such as magnetic resonance imaging, computerized axial tomography, PET, SPECT, photo-acoustic imaging, X-rays and fluorescence imaging/detection. Cancer cell growth can also be determined indirectly, for example by determining the levels of circulating carcino-embryonic antigen, prostate specific antigen or other cancer-specific antigens that are correlated with cancer cell growth.

In particular, efficacy of a combined treatment according to the invention can be assessed by reduction of tumour size, or disappearance of tumour or of any biomarker relevant for a cancer type.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "amino," "alkyl amino," "aminosulfonyl," "ammonium," "alkoxy," "acyl", "acyl amino," "amino carbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of the invention. Examples of such salts include, but are not restricted, to base addition salts formed by reaction of compounds of the invention with organic or inorganic bases such as hydroxide, carbonate, bicarbonate or the like, of a metal cation such as those selected in the group consisting of alkali metals (sodium, potassium or lithium), alkaline earth metals (e.g. calcium or magnesium), or with an organic primary, secondary or tertiary alkyl amine. Other examples of such salts include, but are not restricted, to acid addition salts formed by reaction of compounds of the invention with organic or inorganic acids such as hydrochloric acid, hydrobromic acid, sulphuric acid, para-toluene sulfonic acid, 2-naphtalene sulfonic acid, camphosulfonic acid, benzene sulfonic acid, oxalic acid or the like.

"Pharmaceutically active derivative" refers to any compound that upon administration to the recipient is capable of providing directly or indirectly, the activity disclosed herein.

NOX4/NOX1 Inhibitors According to the Invention

In one embodiment, the invention provides a NOX4 or NOX4/1 or a NOX1 inhibitor presenting an inhibitory constant (Ki) for Nox4 and/or NOX1 ranging from 60 nM or lower to 300 nM in functional assay of ROS production and wherein the inhibitory activity against other NOXs selected from NOX2, 3 and 5 is higher than 1 micromolar.

According to a particular embodiment, NOX4 or NOX4/NOX1 or NOX1 inhibitor according to the invention are pyrazolo pyridine compounds, pyrazoline dione compounds or amido thiazole compounds, such as described in WO 2008/113856, WO 10/035217, WO 10/035219, WO 10/035220, WO 10/035221, WO 11/036651, WO 2013/068972, WO 2015/049655 and WO 2016/098005.

According to another particular embodiment, NOX4 inhibitors according to the invention are 2,5-disubstituted benzoxazole and benzothiazole derivatives such as described in WO 2016/207785.

In one embodiment, the invention provides a NOX4 inhibitor Formula (I)

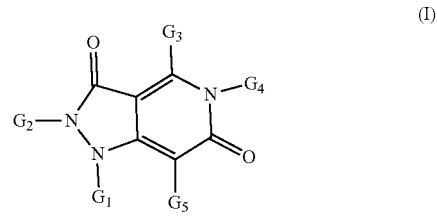

wherein $G_1$ is selected from H, optionally substituted alkyl such as aminocarbonyl alkyl (e.g. phenylacetamide), optionally substituted $C_3$-$C_8$-cycloalkyl alkyl, optionally substituted heterocycloalkyl alkyl, optionally substituted aryl alkyl such as optionally substituted phenyl alkyl like optionally substituted phenyl methyl (e.g. phenyl methyl or 3-methyl phenyl methyl or 4-fluorobenzyl or 2-chlorobenzyl or 4-chlorobenzyl or 4-methyl benzyl or 4-bromobenzyl); and optionally substituted heteroaryl alkyl such as optionally substituted pyridine alkyl like pyridine-2-yl methyl; $G_2$ is selected from H; optionally substituted alkyl; optionally substituted alkenyl; optionally substituted alkynyl; optionally substituted aryl such as optionally substituted phenyl (e.g. phenyl or 4-fluorophenyl or 4-methoxyphenyl or 4-nitrophenyl or 2-chlorophenyl or 2-methyl phenyl or 4-(trifluoromethyl) phenyl or 4-(trifluoromethoxy) phenyl or 2,5-difluorophenyl or 2-methoxyphenyl); optionally substituted alkyl aryl; optionally substituted aryl alkyl; optionally substituted heteroaryl, such as optionally substituted benzothiazolyl (e.g. 1,3-benzothiazol-2-yl) or optionally substituted pyridinyl (e.g. pyridin-2-yl); optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl; $G_3$ is selected from H; optionally substituted alkyl such as methyl or ethyl; optionally substituted alkenyl; optionally substituted alkynyl; optionally substituted aryl such as optionally substituted phenyl (e.g. phenyl); optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl; $G_4$ is selected from H, optionally substituted alkyl such as optionally substituted pentyl (e.g. isopentyl) or optionally substituted heteroalkyl such as optionally substituted methoxy (e.g. 2-methoxyethyl); optionally substituted alkenyl; optionally substituted alkynyl; optionally substituted aryl; optionally substituted alkyl aryl; optionally substituted aryl alkyl such as optionally substituted phenyl methyl (e.g. benzoic acid methyl or benzyl) or optionally substituted phenyl ethyl (e.g. 2-phenyl ethyl, 4-methoxyphenyl ethyl); optionally substituted heteroaryl; optionally substituted alkyl heteroaryl; optionally substituted heteroaryl alkyl such as optionally substituted thiophenyl alkyl like optionally substituted thiophenyl methyl (e.g. thiophen-2-yl methyl) or optionally substituted imidazolyl alkyl like optionally substituted imidazolyl ethyl (e.g. imidazol-4-yl ethyl) or optionally substituted indolyl alkyl like optionally substituted indolyl ethyl (e.g. indol-3-yl ethyl) or optionally substituted furanyl alkyl like optionally substituted furanyl methyl (e.g. furan-2-yl methyl) or optionally substituted benzodioxolyl alkyl like optionally substituted benzodioxolyl methyl (e.g. 1,3-benzodioxol-5-yl methyl) or optionally substituted pyridinyl alkyl like optionally substituted pyridinyl methyl (e.g. pyridine-3-yl methyl or pyridin-2-yl methyl); optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl such as optionally substituted morpholinyl (e.g. 5-morpholin-4-yl) or optionally substituted piperazinyl (e.g. 4-methyl piperazinyl) or optionally substituted piperidinyl (e.g. 4-methylbenzyl)piperidin-4-yl); optionally substituted alkyl $C_3$-$C_8$-cycloalkyl; and optionally substituted $C_3$-$C_8$-cycloalkyl alkyl; optionally substituted alkyl heterocycloalkyl and optionally substituted heterocycloalkyl alkyl such as optionally substituted morpholinyl alkyl like optionally substituted morpholinyl propyl (e.g. 3-(morpholin-4-yl) propyl)) optionally substituted morpholinyl ethyl (e.g. 2-morpholin-4-ylethyl); or optionally substituted piperazinyl alkyl like optionally substituted piperazinyl ethyl (e.g. 2-(4-acetylpiperazin-1-yl) ethyl or 2-(4-hexanoyl piperazin-1-yl) ethyl) or optionally substituted pyrrolidinyl alkyl like optionally substituted pyrrolidinyl propyl (e.g. 3-(2-oxopyrrolidin-1-yl) propyl) or optionally substituted tetrahydrofuranyl alkyl like optionally substituted tetrahydrofuranyl methyl (e.g. tetrahydrofuran-2-yl methyl); $G_5$ is selected from H, optionally substituted alkyl; optionally substituted alkenyl; optionally substituted alkynyl; optionally substituted aryl; optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl; as well as pharmaceutically acceptable salts and pharmaceutically active derivative thereof.

In another embodiment, the invention provides a NOX4/1 inhibitor Formula (II)

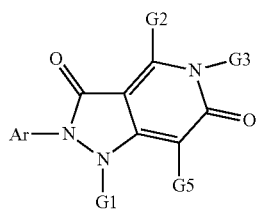

(II)

wherein Ar is optionally substituted phenyl such as phenyl optionally substituted by halogen such as chloro (e.g. 2-chlorophenyl) or by alkoxy (e.g. methoxy); $G_1$ and $G_4$ are H; $G_2$ is selected from optionally substituted $C_1$-$C_6$ alkyl (e.g. methyl) and optionally substituted phenyl (such as phenyl optionally substituted by halogen such as 3-chlorophenyl, 4-chlorophenyl, 2-fluorophenyl, 3-fluorophenyl, 4-fluorophenyl, 4-chloro-2-fluorophenyl, 5-chloro-2-fluorophenyl, phenyl optionally substituted by amino or alkyl amino or alkoxy such as 3-dimethylaminophenyl, 2-trimethyl amino phenyl, 3-methyl amino phenyl, 3-amino phenyl, 4-methoxy phenyl); $G_3$ is selected from H, optionally substituted $C_1$-$C_6$ alkyl (e.g. methyl, $C_1$-$C_6$ alkyl substituted by alkoxy like methoxy ethyl such as 2-methoxyethyl), optionally substituted heteroaryl $C_1$-$C_6$ alkyl like optionally substituted pyridinyl $C_1$-$C_6$ alkyl (e.g. optionally substituted pyridinyl methyl like pyridinyl-2ylmethyl, pyridinyl-3ylmethyl, 6-methoxypyridin-3-yl methyl, 2-methoxypyridin-4-yl methyl) or optionally substituted pyrazinyl $C_1$-$C_6$ alkyl (e.g. pyrazinyl-2-ylmethyl) and optionally substituted alkoxy $C_1$-$C_6$ alkyl such as methoxy ethyl (e.g. 2 methoxyethyl) or $G_2$ and $G_3$ form together an optionally substituted 7-membered heterocycloalkyl ring comprising two nitrogen atoms, and where the two nitrogens are attached through a optionally substituted $C_1$-$C_3$ alkyl moiety, as well as tautomers, geometrical isomers, optically active forms and pharmaceutically acceptable salts thereof.

In a particular embodiment, the invention provides a NOX4/1 inhibitor of Formula (II) wherein $G_2$ and $G_3$ form together an optionally substituted 7-membered heterocycloalkyl ring comprising two nitrogen atoms to form the following compound of Formula (I'):

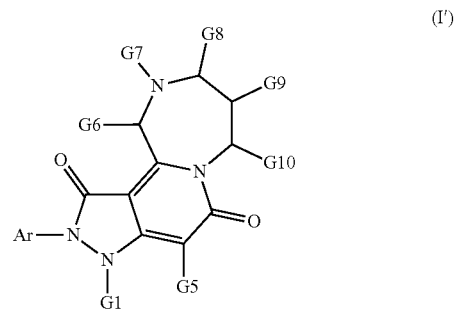

(I')

wherein Ar, $G_1$ and $G_5$ are as defined herein; $G_6$, $G_8$ to $G_{10}$ are H; $G_7$ is selected from optionally substituted $C_1$-$C_6$ alkyl such as $C_1$-$C_6$ alkyl optionally substituted with optionally substituted phenyl (e.g. methyl optionally substituted with optionally substituted phenyl such as benzyl, methyl optionally substituted with phenyl substituted by halogen such as 2-chlorobenzyl, 3-chlorobenzyl, 4-chlorobenzyl, methyl optionally substituted with phenyl substituted by alkoxy such as 2-methoxybenzyl, 3-methoxybenzyl, 4-methoxybenzyl), optionally substituted aryl $C_1$-$C_6$ alkyl such as optionally substituted phenyl $C_1$-$C_6$ alkyl (e.g. benzyl, 2-chlorobenzyl, 3-chlorobenzyl, 4-chlorobenzyl, 2-methoxybenzyl, 3-methoxybenzyl, 4-methoxybenzyl) and optionally substituted heteroaryl $C_1$-$C_6$ alkyl such as optionally substituted pyridinyl $C_1$-$C_6$ alkyl (e.g. optionally substituted pyridinyl methyl like pyridinyl-2ylmethyl, pyridinyl-3ylmethyl) or optionally substituted furanyl $C_1$-$C_6$ alkyl (e.g. optionally substituted furanyl methyl like furan-3ylmethyl) as well as tautomers, geometrical isomers, optically active forms and pharmaceutically acceptable salts thereof.

In a particular embodiment, the invention provides a compound of Formula (II) for use according to the invention wherein $G_2$ is optionally substituted $C_1$-$C_6$ alkyl.

In another particular embodiment, the invention provides a compound of Formula (II) for use according to the invention wherein $G_2$ is optionally substituted phenyl.

In another particular embodiment, the invention provides a compound of Formula (II) for use according to the invention wherein $G_3$ is optionally substituted $C_1$-$C_6$ alkyl.

In another particular embodiment, the invention provides a compound of Formula (II) for use according to the invention wherein $G_3$ is optionally substituted heteroaryl $C_1$-$C_6$ alkyl like optionally substituted pyridinyl $C_1$-$C_6$ alkyl.

In another particular embodiment, the invention provides a compound of Formula (II) for use according to the invention wherein $G_2$ and $G_3$ form together an optionally substituted 7-membered heterocycloalkyl ring comprising two nitrogen atoms to form the following compound of Formula (I'), wherein G7 is optionally substituted $C_1$-$C_6$ alkyl.

In another the invention provides a compound of Formula (II) for use according to the invention wherein $G_2$ and $G_3$ form together an optionally substituted 7-membered heterocycloalkyl ring comprising two nitrogen atoms to form the following compound of Formula (I'), wherein G7 is optionally substituted aryl $C_1$-$C_6$ alkyl.

In another the invention provides a compound of Formula (I) for use according to the invention wherein $G_2$ and $G_3$ form together an optionally substituted 7-membered heterocycloalkyl ring comprising two nitrogen atoms to form the following compound of Formula (I'), wherein $G_7$ is optionally substituted heteroaryl $C_1$-$C_6$ alkyl.

According to another particular embodiment, NOX1 inhibitors according to the invention are amido thiazole derivatives such as described in WO 2016/098005.

In another embodiment, is provided a NOX1 inhibitor of Formula (III):

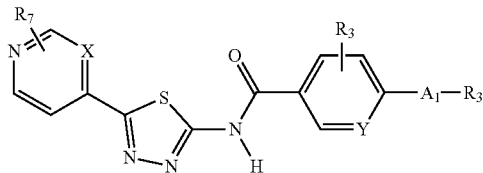

(III)

wherein X is selected from $CR^1$ and N; Y is selected from CH or N; $A_1$ is selected from —$OCHR^5$—, —$NR^4$—$CHR^5$—, —$CH_2NR^4$— and —$CH_2$—O—; le is selected from H, halogen and optionally substituted $C_1$-$C_6$ alkyl; $R^2$ is selected from H, halogen (e.g. chloro, fluoro), optionally substituted alkoxy such optionally substituted methoxy (e.g. methoxy, (tetrahydro-2H-pyran-4-yl)methoxy, piperidin-4-ylmethoxy) or optionally substituted ethoxy (e.g. 2-(dimethylamino)ethoxy, 2-hydroxy ethoxy, 1-phenylethoxy, 2-methoxy ethoxy), optionally substituted alkoxy $C_1$-$C_6$ alkyl, optionally substituted $C_1$-$C_6$ alkyl such as optionally substituted methyl, optionally substituted amino such as optionally substituted $C_1$-$C_6$ alkyl amino (e.g. methyl amino, tetrahydro-2H-pyran-4-yl)methyl)amino, (1-methylpiperidin-4-yl)methyl)amino, di-methyl amino, optionally substituted ethyl amino such as 2-morpholino ethyl amino or 2-(dimethylamino) ethyl amino or methoxy ethyl amino, optionally substituted methyl amino such as 1-methyl-1H-imidazol-4-yl methyl amino or 2-hydroxyethyl)amino, optionally substituted propyl amino such as dimethylamino propyl amino), optionally substituted heterocycloalkyl such as optionally substituted piperazine (e.g. methylpiperazin-1-yl), optionally substituted $C_1$-$C_6$ alkyl heterocycloalkyl such as optionally substituted $C_1$-$C_6$ alkyl piperazine (e.g. methylpiperazin-1-yl), optionally substituted amino $C_1$-$C_6$ alkyl, optionally substituted alkoxy $C_1$-$C_6$ alkyl, —O—$R^8$ and —$NR^9R^{10}$; $R^3$ is a group of formula —$(CHR^6)_n$-$A_2$ or $R^3$ forms with the moiety $CHR^5$ from $A_1$ an optionally substituted ring selected from optionally substituted aryl such as an optionally substituted phenyl (e.g. phenyl or phenyl substituted by halogen such as fluoro phenyl substituted by alkoxy such as methoxy) and optionally substituted heteroaryl such as optionally substituted 1,3-dihydro-1H-indenyl (e.g. 1-(dimethylamino)-2,3-dihydro-1H-inden-2-yl, 2,3-dihydro-1H-inden-2-yl, 2,3-dihydro-1H-inden-1-yl) or optionally substituted 6,7-dihydro-5H-cyclopenta pyridinyl (e.g. 6,7-dihydro-5H-cyclopenta[b]pyridin-5-yl, 2-methylpyridin-3-yl, 5-methylpyridin-2-yl) or optionally substituted 1,2,3,4-tetrahydronaphthalenyl (e.g. 1,2,3,4-tetrahydronaphthalen-1-yl) or optionally substituted 2,3-dihydrobenzofuranyl (e.g. 2,3-dihydrobenzofuran-3-yl, 2,3-dihydro-1H-inden-1-yl) or optionally substituted thiadiazolyl (e.g. 1,3,4-thiadiazol-2-yl) or optionally substituted isoxazolyl (e.g. 5-methylisoxazol-3-yl) or optionally substituted pyrazolyl (e.g. 1-methyl-1H-pyrazol-3-yl) or optionally substituted imidazolyl (e.g. 1-methyl-1H-imidazol-2-yl), or $R^3$ forms with the moiety $NR^4$ from $A_1$ an optionally substituted ring selected from optionally substituted aryl and optionally substituted heteroaryl such as optionally substituted isoindolinyl (e.g. isoindolin-2-yl, 1H-indol-1-yl)); n is an integer from 0 to 4 (such as 0, 1, 2, 3 or 4); $R^4$ is selected from H and optionally substituted alkyl such as optionally substituted methyl; $A_2$ is an optionally substituted ring selected from optionally substituted aryl such as optionally substituted phenyl (e.g. methoxy phenyl, fluoro phenyl, chloro phenyl), optionally substituted heteroaryl such as optionally substituted pyridin (e.g. pyridin-2-yl, pyridin-3-yl, pyridin-4-yl, 2-methyl pyridin-3-yl, 5-methyl pyridin-2-yl) or optionally substituted pyrazolyl (e.g. 1,3-dimethyl-1H-pyrazol-5-yl, 1-methyl-1H-pyrazol-3-y) or optionally substituted thiadiazolyl (e.g. 1,3,4-thiadiazol-2-yl) or optionally substituted imidazolyl (e.g. 1H-imidazol-4-yl, 1-methyl-1H-imidazol-2-yl, 1-methyl-1H-imidazol-5-yl) or optionally substituted 1,2,4-triazolyl (e.g. 1-methyl-1H-1,2,4-triazol-5-yl) or optionally substituted isoxazolyl (e.g. 1-cyclopropylisoxazol-3-yl) or optionally substituted oxadiazolyl (e.g. 5-methyl-1,2,4-oxadiazol-3-yl) or optionally substituted pyrimidinyl (e.g. pyrimidinyl-2-yl); $R^5$ is selected from H, optionally substituted $C_1$-$C_6$ alkyl such as optionally substituted methyl (e.g. methoxy methyl, 3,3-difluoropyrrolidin-1-yl methyl, 4-methylpiperazin-1-yl methyl, hydroxyl methyl) or optionally substituted ethyl or optionally substituted propyl (e.g. methyl, hydroxy methyl, hydroxy ethyl, 2-propanoyl, hydroxyl isopropyl), optionally substituted amino $C_1$-$C_6$ alkyl such as optionally substituted amino methyl (e.g. dimethylamino methyl, methylamino methyl), optionally substituted alkoxy $C_1$-$C_6$ alkyl, optionally substituted heterocycloalkyl $C_1$-$C_6$ alkyl such as optionally substituted heterocycloalkyl methyl for example optionally substituted pyrrolidin $C_1$-$C_6$ alkyl (e.g. 3,3-difluoropyrrolidin-1-yl methyl) or substituted piperazine $C_1$-$C_6$ alkyl (e.g. 4-methylpiperazin-1-yl methyl) or heterocycloalkyl ethyl for example optionally substituted morpholino $C_1$-$C_6$ alkyl (e.g. morpholino methyl, morpholino ethyl) or optionally substituted pyrrolidin $C_1$-$C_6$ alkyl (e.g. pyrrolidin methyl, pyrrolidin ethyl), optionally substituted aminocarbonyl (e.g. dimethyl aminocarbonyl), optionally substituted $C_2$-$C_8$ cycloalkyl such as optionally substituted cyclopropyl and optionally substituted amino $C_1$-$C_6$ alkyl such as optionally substituted amino ethyl (e.g. di-methyl amino ethyl) or optionally substituted amino methyl (e.g. di-methyl amino methyl); $R^6$ is selected from H, optionally substituted $C_1$-$C_6$ alkyl such as optionally substituted methyl, optionally substituted amino optionally substituted $C_1$-$C_6$ alkyl amino (e.g. dimethyl amino) and hydroxy and wherein $R^6$ groups are independently selected for each repeating unit (CHR$^6$); $R^7$ is selected from H, halogen (e.g. fluoro) and optionally substituted $C_1$-$C_6$ alkyl such as methyl; $R^8$ is selected from H, optionally substituted $C_1$-$C_6$ alkyl such as optionally substituted methyl or optionally substituted ethyl (e.g. methoxy ethyl, 2-(dimethylamino) ethyl, hydroxy ethyl), optionally substituted amino $C_1$-$C_6$ alkyl, optionally substituted heterocycloalkyl, optionally substituted $C_2$-$C_8$ cycloalkyl, optionally substituted heterocycloalkyl $C_1$-$C_6$ alkyl such as optionally substituted heterocycloalkyl methyl, for example optionally substituted tetrahydropyran $C_1$-$C_6$ alkyl (e.g. tetrahydro-2H-pyran-4-yl) or optionally substituted piperidine alkyl (e.g. 1-methylpiperidin-4-yl), optionally substituted $C_2$-$C_8$ cycloalkyl $C_1$-$C_6$ alkyl, optionally substituted alkoxy, optionally substituted amino $C_1$-$C_6$ alkyl such optionally substituted amino ethyl (e.g. 2-(dimethylamino)ethyl); optionally substituted aryl $C_1$-$C_6$ alkyl and optionally substituted heteroaryl $C_1$-$C_6$ alkyl; $R^9$ and $R^{10}$ are independently selected from H, optionally substituted $C_1$-$C_6$ alkyl such a optionally substituted methyl (e.g. 1-methyl-1H-imidazol-4-yl)methyl)) or optionally substituted ethyl (e.g. 2-methoxy ethyl), optionally substituted amino $C_1$-$C_6$ alkyl such as optionally substituted amino ethyl (e.g. dimethyl amino ethyl) or such as optionally substituted amino propyl (e.g. dimethylamino)propyl), optionally substituted heterocycloalkyl such as optionally substituted piperidine (e.g. 1-methylpiperidin), optionally substituted $C_2$-$C_8$ cycloalkyl, optionally substituted heterocycloalkyl $C_1$-$C_6$ alkyl such as optionally substituted heterocycloalkyl ethyl for example optionally substituted morpholino $C_1$-$C_6$ alkyl (e.g. 2-morpholino ethyl) or optionally substituted heterocycloalkyl methyl for example optionally substituted tetrahydrofuran $C_1$-$C_6$ alkyl (e.g. tetrahydro-2H-pyran-4-yl methyl) or piperidin $C_1$-$C_6$ alkyl (e.g. 1-methylpiperidin-4-yl) methyl or optionally substituted imidazoyl $C_1$-$C_6$ alkyl (e.g. 1-methyl-1H-imidazol-4-yl)methyl)optionally substituted $C_2$-$C_5$ cycloalkyl $C_1$-$C_6$ alkyl, optionally substituted alkoxy, optionally substituted alkoxy $C_1$-$C_6$ alkyl such as optionally substituted alkoxy ethyl (e.g. 2-methoxy ethyl), optionally substituted aryl $C_1$-$C_6$ alkyl and optionally substituted heteroaryl $C_1$-$C_6$ alkyl such as heteroaryl $C_1$-$C_6$ alkyl methyl, for example optionally substituted imidazolyl $C_1$-$C_6$ alkyl (e.g. 1-methyl-1H-imidazol-4-yl methyl), optionally substituted amino $C_1$-$C_6$ alkyl such optionally substituted amino ethyl or optionally substituted amino propyl (e.g. 2-(dimethylamino)ethyl, 2-(dimethylamino) propyl)); as well as tautomers, geometrical isomers, optically active forms, pharmaceutically acceptable salts and pharmaceutically active derivative thereof.

In a particular embodiment, the invention provides a compound of Formula (III) for use according to the invention wherein X is CH.

In a particular embodiment, the invention provides a compound of Formula (III) for use according to the invention wherein Y is CR$^1$, in particular CH.

In a particular embodiment, the invention provides a compound of Formula (III) for use according to the invention wherein R$^2$ is optionally substituted alkoxy (e.g. methoxy).

In a particular embodiment, the invention provides a compound of Formula (III) for use according to the invention wherein R$^7$ is H.

In a particular embodiment, the invention provides a compound of Formula (III) for use according to the invention wherein $A_1$ is —OCHR$^5$, in particular wherein R$^5$ is an optionally substituted morpholino $C_1$-$C_6$ alkyl (e.g. morpholino methyl).

In another particular embodiment, the invention provides a compound of Formula (III) for use according to the invention wherein $A_1$ is —OCHR$^5$, in particular wherein R$^5$ is an optionally substituted amino $C_1$-$C_6$ alkyl (e.g. di-methyl amino methyl).

In another particular embodiment, the invention provides a compound of Formula (III) for use according to the invention wherein $A_1$ is —OCHR$^5$, in particular wherein R$^5$ is an optionally substituted hydroxyl $C_1$-$C_6$ alkyl (e.g. hydroxy methyl).

In a particular embodiment, the invention provides a compound of Formula (III) for use according to the invention wherein R$^3$ is a group of formula —(CHR$^6$)$_n$-$A_2$, in particular wherein n is 0 and $A_2$ is optionally substituted phenyl (e.g. phenyl).

According to another particular embodiment, a NOX1 inhibitor according to the invention is 3-methoxy-4-(2-morpholino-1-phenylethoxy)-N-(5-(pyridin-4-yl)-1,3,4-thiadiazol-2-yl)benzamide, in particular (R) 3-methoxy-4-(2-morpholino-1-phenylethoxy)-N-(5-(pyridin-4-yl)-1,3,4-thiadiazol-2-yl)benzamide.

In another embodiment, is provided a NOX4 inhibitor of Formula (IV):

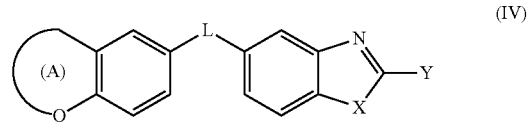

(IV)

wherein ring (A) represents a non-aromatic 5- to 7-membered heterocyclic ring which is fused to the phenyl group; wherein said 5- to 7-membered heterocyclic ring contains one oxygen ring atom and optionally one further ring heteroatom independently selected from oxygen or nitrogen; wherein said 5- to 7-membered heterocyclic ring independently is unsubstituted, or mono-, or di-substituted, wherein the substituents are independently selected from:
  one oxo substituent attached to a ring carbon atom in alpha position to a ring oxygen and/or a ring nitrogen atom; and 1 or
  one $C_{1-3}$-alkyl attached to a ring nitrogen atom having a free valency; or
  two fluoro substituents attached to the same ring carbon atom;
  L represents —NH—CO—* or —CO—NH—*, wherein the asterisks (*) indicate the bond that is linked to the benzoxazole 1 the benzothiazole moiety; X represents 0 or S; and
  Y represents
  —NR$^1$R$^2$ wherein R$^1$ represents $C_{1-4}$-alkyl; $C_{2-4}$-alkyl which is mono-substituted with di-($C_{1-3}$-alkyl)amino, hydroxy or $C_{1-3}$-alkoxy; $C_{3-5}$-cycloalkyl-L$^1$, wherein L$^1$ represents a direct bond or $C_{1-3}$-alkylene; and wherein the $C_{3-5}$-cycloalkyl optionally contains one oxygen ring atom, and wherein said $C_{3-5}$-cycloalkyl is unsubstituted, or mono-substituted with methyl or fluoro; or a piperidin-3-yl, piperidin-4-yl or pyrrolidin-3-yl group, which groups are substituted on the ring nitrogen atom with $C_{3-5}$-cycloalkyl, wherein said $C_{3-5}$-cycloalkyl optionally contains one oxygen ring atom; and $R^2$ represents hydrogen, $C_{1-3}$-alkyl, or $C_{3-5}$-cycloalkyl; or Y represents a saturated 4- to 7-membered monocyclic heterocyclyl selected from morpholin-4-yl; 2-oxo-pyrrolidin-1-yl; 1, 1-dioxidothiomorpholin-4-yl; or piperazin-1-yl optionally mono-substituted in position 4 with oxetan-3-yl or $C_{1-3}$-alkyl; or azetidin-1-yl, pyrrolidin-1-yl, or piperidin-1-yl; wherein said azetidin-1-yl, pyrrolidin-1-yl, or piperidin-1-yl independently is unsubstituted, or substituted with:

two fluoro substituents attached to the same ring carbon atom; or one substituent selected from unsubstituted phenyl, or unsubstituted or 6-membered heteroaryl; or one substituent selected from hydroxy; $C_{1-3}$-alkoxy; —CO—$C_{1-4}$-alkoxy; di($C_{1-3}$-alkyl)amino; and $C_{1-3}$-alkyl which is mono-substituted with di-($C_{1-3}$-alkyl)amino, hydroxy, or $C_{1-3}$-alkoxy; or two substituents, wherein one of said substituents is $C_{1-4}$-alkyl, and the other is independently selected from hydroxy, or di-($C_{1-3}$-alkyl)amino; or one substituent selected from morpholin-4-yl; 1, 1-dioxidothiomorpholin-4-yl; or piperazin-1-yl which is optionally mono-substituted in position 4 with $C_{1-3}$-alkyl;

one substituent selected from azetidin-1-yl, pyrrolidin-1-yl, or piperidin-1-yl; wherein said groups independently are unsubstituted, or mono-substituted with hydroxy, or di-substituted with methyl and hydroxy;

or Y represents saturated 7- to 11-membered fused, bridged, or spiro-bicyclic heterocyclyl containing at least one nitrogen atom, wherein said nitrogen atom is bound to the benzoxazole/the benzothiazole moiety, and wherein said heterocyclyl optionally contains one further ring heteroatom independently selected from oxygen, nitrogen and sulfur; wherein said heterocyclyl is unsubstituted, or substituted with:

two oxo substituents at a ring sulfur ring atom; or one $C_{1-3}$-alkyl substituent attached to a ring nitrogen atom having a free valency;

or a pharmaceutically acceptable salt thereof.

In another particular embodiment, is provided compound of Formula (I) for use according to the invention, wherein the compound is

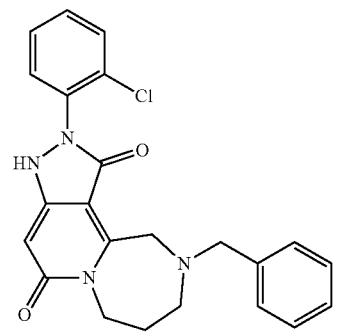

2-(2-chlorophenyl)-4-methyl-5-(pyridin-2-ylmethyl)-1H-pyrazolo[4,3-c]pyridine-3,6(2H,5H)-dione.

In another particular embodiment, is provided compound of Formula (I) for use according to the invention, wherein the compound is

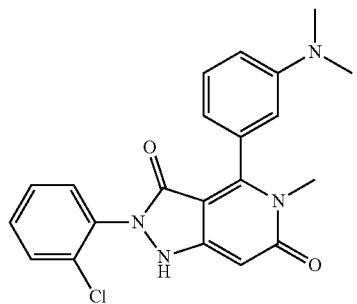 [SMILES: CN(C)c1cccc(-c2c3c(=O)n(-c4ccccc4Cl)[nH]c3cc(=O)n2C)c1]

2-(2-chlorophenyl)-4-[3-(dimethylamino)phenyl]-5-methyl-1H-pyrazolo[4,3-c]pyridine-3,6(2H,5H)-dione.

In another particular embodiment, is provided compound of Formula (I) for use according to the invention, wherein the compound is

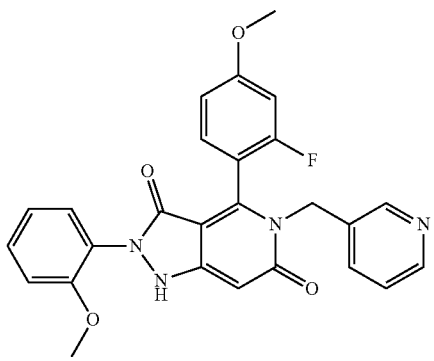 [SMILES: COc1ccc(-c2c3c(=O)n(-c4ccccc4OC)[nH]c3cc(=O)n2Cc2cccnc2)c(F)c1]

4-(2-fluoro-4-methoxyphenyl)-2-(2-methoxyphenyl)-5-(pyridin-3-ylmethyl)-1H-pyrazolo[4,3-c]pyridine-3,6(2H,5H)-dione.

In another particular embodiment, is provided compound of Formula (I') for use according to the invention, wherein the compound is 10-benzyl-2-(2-chlorophenyl)-2,3,8,9,10,11-hexahydro-1H-pyrazolo[4',3':3,4]pyrido[1,2-a][1,4]diazepine-1,5(7H)-dione.

In another particular embodiment, is provided compound of Formula (IV) for use according to the invention, wherein the compound

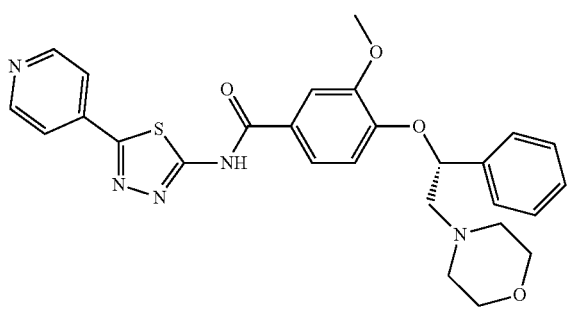 [SMILES: COc1cc(C(=O)Nc2nnc(-c3ccncc3)s2)ccc1O[C@@H](CN1CCOCC1)c1ccccc1]

(R)-3-methoxy-4-(2-morpholino-1-phenylethoxy)-N-(5-(pyridin-4-yl)-1,3,4-thiadiazol-2-yl)benzamide.

In another particular embodiment, is provided compound of Formula (IV) for use according to the invention, wherein the compound is:

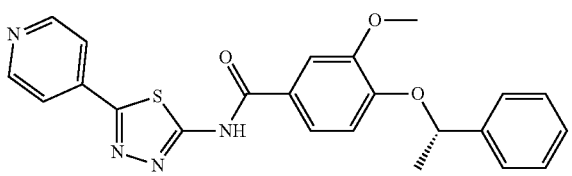 [SMILES: COc1cc(C(=O)Nc2nnc(-c3ccncc3)s2)ccc1O[C@@H](C)c1ccccc1]

(S)-3-methoxy-4-(1-phenylethoxy)-N-(5-(pyridin-4-yl)-1,3,4-thiadiazol-2-yl)benzamide.

In another particular embodiment, is provided compound of Formula (IV) for use according to the invention, wherein the compound is:

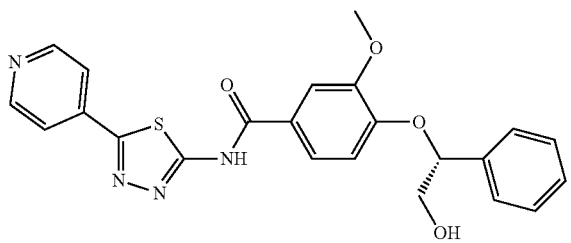 [SMILES: COc1cc(C(=O)Nc2nnc(-c3ccncc3)s2)ccc1O[C@@H](CO)c1ccccc1]

(R)-4-(2-hydroxy-1-phenylethoxy)-3-methoxy-N-(5-(pyridin-4-yl)-1,3,4-thiadiazol-2-yl)benzamide.

In another particular embodiment, is provided compound of Formula (IV) for use according to the invention, wherein the compound is:

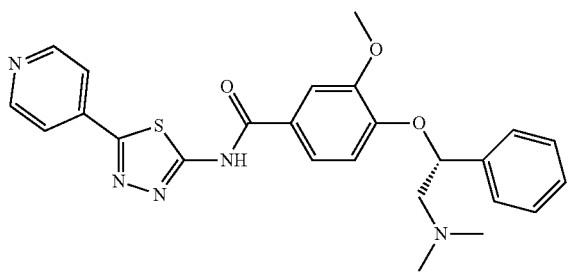 [SMILES: COc1cc(C(=O)Nc2nnc(-c3ccncc3)s2)ccc1O[C@@H](CN(C)C)c1ccccc1]

(R)-4-(2-(dimethylamino)-1-phenylethoxy)-3-methoxy-N-(5-(pyridin-4-yl)-1,3,4-thiadiazol-2-yl)benzamide.

In another particular embodiment, is provided a compound according to the invention selected from the following group:

2-(2-chlorophenyl)-4-methyl-5-(pyridin-2-ylmethyl)-1H-pyrazolo[4,3-c]pyridine-3,6(2H,5H)-dione;

2-(2-chlorophenyl)-4-[3-(dimethylamino)phenyl]-5-methyl-1H-pyrazolo[4,3-c]pyridine-3,6(2H,5H)-dione;

4-(2-fluoro-4-methoxyphenyl)-2-(2-methoxyphenyl)-5-(pyridin-3-ylmethyl)-1H-pyrazolo[4,3-c]pyridine-3,6(2H,5H)-dione;

(R)-3-methoxy-4-(2-morpholino-1-phenylethoxy)-N-(5-(pyridin-4-yl)-1,3,4-thiadiazol-2-yl)benzamide;

10-benzyl-2-(2-chlorophenyl)-2,3,8,9,10,11-hexahydro-1H-pyrazolo[4',3':3,4]pyrido[1,2-a][1,4]diazepine-1,5(7H)-dione;

(S)-3-methoxy-4-(1-phenylethoxy)-N-(5-(pyridin-4-yl)-1,3,4-thiadiazol-2-yl) benzamide;

(R)-4-(2-hydroxy-1-phenylethoxy)-3-methoxy-N-(5-(pyridin-4-yl)-1,3,4-thiadiazol-2-yl)benzamide and (R)-4-(2-(dimethylamino)-1-phenylethoxy)-3-methoxy-N-(5-(pyridin-4-yl)-1,3,4-thiadiazol-2-yl)benzamide.

According to a particular aspect is provided a NOX inhibitor selected from a NOX4 inhibitor and a NOX4/1 inhibitor for use in combination with a cancer vaccine or with at least one immune checkpoint inhibitor.

According to a further particular aspect is provided a NOX inhibitor selected from a NOX4 inhibitor and a NOX4/1 inhibitor for use in combination with a cancer vaccine or with at least one immune checkpoint inhibitor.

According to another further particular aspect is provided a NOX inhibitor selected from a NOX4 inhibitor and a NOX4/1 inhibitor for use in combination with a cancer vaccine.

According to another further particular aspect is provided a NOX inhibitor selected from a NOX1 inhibitor and a NOX1/4 inhibitor for use in combination with at least one an anti-angiogenic agent.

Anti-Cancer Immunotherapeutic Agents According to the Invention

An anti-cancer immunotherapeutic agent that can be used according to the invention encompass cancer vaccines such as oncolytic or anti-Herpes simplex virus vaccines such as described in Bartlett et al., 2013, *Molecular Cancer* 2, 12:103 (e.g. talimogene laherparepvec (Imlygic)) or in Fukuhara et al., 2016, *Cancer Sci*, 107(10), 1373-1379, adoptive cellular immunotherapy such as described in Perica et al., 2015, *Rambam Maimonides Med J*, 6(1), e0004, immune checkpoint inhibitors such as PD-1 inhibitors like those described in Iwai et al., 2017, *Journal of Biomedical Science*, 24:26 or Mishra, 2017, *Future Oncol. doi:* 10.2217/fon-2017-0115 or Soto Chervin et al., 2016, *F1000Research* 2016, 5(F1000 *Faculty Rev*):803 (e.g. such as Pembrolizumab (Keytruda), Nivolumab (Opdivo)), or PD-L1 inhibitors like Atezolizumab (Tecentriq), Avelumab (Bavencio), Durvalumab (Imfinzi) or CTLA-4 inhibitors such as Ipilimumab (Yervoy).

According to another particular aspect, an immune checkpoint inhibitor according to the invention may be selected from T cell immunoglobulin and mucin domain 3 (TIM3), Lymphocyte activation gene-3 (LAG3), T-cell immunoglobulin and ITIM domains (TIGIT) or B- and T-lymphocyte attenuator (BTLA) inhibitors.

According to a particular aspect, an immune checkpoint inhibitor according to the invention is a PD-1 inhibitor.

According to a particular aspect, an anti-cancer vaccine according to the invention encompasses DNA, RNA, peptide and oncolytic virus vaccines.

Further, more generally, since infiltration of CD8+ T-cells into tumours is fundamental to most immunotherapies, combinations and combined uses according to the invention would also be useful in adoptive T-cell transfer therapies, including tumour infiltrating lymphocytes (TILs), T cell receptor (TCR) T-cells and chimeric antigen receptor (CAR)-T-cells such as described in June et al., 2018, *Science*, 359: 1361-1365. TILs have been shown to induce durable, complete responses in patients with metastatic melanoma. CAR T-cells have produced significant benefit in the treatment of haematological malignancies (Kochenderfer et al. 2010., *Blood* 116, 4099-4102; Porter et al., 2011, *N. Engl. J. Med.*, 365, 725-733; Brentjens et al., 2013, *Sci. Transl. Med.*, 5, 177ra38; Grupp et al., 2013, *N. Engl. J. Med.*, 368, 1509-1518), however, the tumour microenvironment remains a significant barrier to success in solid cancers.

Similarly, immunotherapeutic agent that can be used according to the invention encompass CD8+ T-cell agonists, such as α-CD40, α-CD27, α-41BB, α-OX40, GITR.

Anti-Angiogenic Agents for Used in a Combination According to the Invention

An antiangiogenic agent that can be used according to the invention encompass anti-VEGF agents such as described in Gardner et al., 2017, supra, in particular bevacizumab or sunitinib.

Compositions

The invention provides pharmaceutical or therapeutic agents as compositions and methods for treating a patient, preferably a mammalian patient, and most preferably a human patient who is suffering from a solid tumor cancer presenting or susceptible to present a resistance to immunotherapy or to an anti-angiogenic agent, in particular to an anti-VEGF treatment.

Pharmaceutical compositions of the invention can contain one or more compound in any form described herein. Compositions of this invention may further comprise one or more pharmaceutically acceptable additional ingredient(s), such as alum, solubilizers, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as powder in sachets, tablets or filled capsules, or liquids such as solutions, suspensions, emulsions, elixirs, nasal spray, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably oral, sublingual, nasal and subcutaneous.

Compositions of this invention may also be liquid formulations, including, but not limited to, aqueous or oily suspensions, solutions, emulsions, syrups, spray and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in *The Science and Practice of Pharmacy* (Remington: The Science & Practice of Pharmacy), 22$^{nd}$ Edition, 2012, Lloyd, Ed. Allen, Pharmaceutical Press, which is incorporated herein by reference. Solid compositions of this invention may be in the form of powder in sachets, tablets or lozenges formulated in a conventional manner. For example, sachets, tablets and capsules for oral or sublingual administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, via buccal administration, nasally, intralesionally or combinations thereof. Parenteral administration includes, but is not limited to subcutaneous and intramuscular. The compositions of this invention may also be administered in the form of an implant, which allows slow release of the compositions as well as a slow controlled i.v. infusion. In a particular embodiment, one or more NOX4, NOX4/1 or NOX1 inhibitor is administered orally.

The dosage administered, as single or multiple doses, to an individual will vary depending upon a variety of factors, including pharmacokinetic properties, patient conditions and characteristics (age, body weight, health, body size), extent of symptoms, frequency of treatment and the effect desired.

Combination

According to one embodiment of the invention, a NOX4, NOX4/1 or a NOX1 inhibitor according to the invention and pharmaceutical formulations thereof is to be administered in combination with an anti-cancer immunotherapeutic agent, in particular an anticancer vaccine or at least one immune check point inhibitor such as at least one PD-1, PD-L1 or CTLA4 inhibitor.

The invention encompasses the administration of a NOX4, NOX4/1 or NOX1 inhibitor or a pharmaceutical formulation thereof, wherein NOX4/1 inhibitor or a pharmaceutical formulation thereof is administered to an individual prior to, or simultaneously with an anti-cancer immunotherapeutic agent, for example concomitantly through the same formulation or separately through different formulations, in particular through different formulation routes.

According to a particular aspect of the invention, a NOX4, NOX4/1 or NOX1 inhibitor according to the invention and pharmaceutical formulations thereof is to be administered chronically (e.g. daily or weekly) for the duration of treatment and prior to the administration of an anti-cancer immunotherapeutic agent or the anti-angiogenic treatment.

According to another particular aspect of the invention, a NOX4, NOX4/1 or NOX1 inhibitor according to the invention and pharmaceutical formulations thereof is to be administered concomitantly with an anti-cancer immunotherapeutic agent.

According to another particular aspect of the invention, the anti-cancer immunotherapeutic agent can be administered in combination with other therapeutic regimens or co-agents useful in the treatment of cancer (e.g. multiple drug regimens), in a therapeutically effective amount, such as in combination with substances useful for treating, stabilizing, preventing, and/or delaying cancer such as substances used in conventional chemotherapy directed against solid tumors and for control of establishment of metastases or any other molecule that act by triggering programmed cell death e.g. for example a co-agent selected from angiogenesis inhibitors (e.g. anti-VEGF agents such as described in Gardner et al., 2017, supra), immunotherapy agents (e.g. recombinant cytokines, interferones, interleukin, recombinant antibodies such as Herceptin®) and chemotherapeutic agents (e.g. cisplatin, paclitaxel, methotrexate, 5-fluoruracil, Gemcitabin, Vincristin, Vinblastin, Doxorubicin, Temozolomide). In particular, According to another particular aspect of the invention, the anti-cancer immunotherapeutic agent can be administered in combination with other therapeutic regimens or co-agents useful in the treatment of cancer (e.g. multiple drug regimens), in a therapeutically effective amount, such as in combination with at least one inhibitor of vascular endothelial growth factor (VEGF) (e.g. bevacizumab, sunitinib inhibitors), at least one inhibitor of basic fibroblast growth factor (bFGF) or at least one inhibitor of hypoxia-inducible factor-1 (HIF-1).

NOX4/1 inhibitor or the pharmaceutical formulations thereof that are administered simultaneously with said anti-cancer immunotherapeutic agent can be administered in or within the same or different composition(s) and by the same or different route(s) of administration.

Patients

In one embodiment, subjects according to the invention are subjects suffering from a solid tumor cancer, in particular a poorly responsive solid tumor cancer presenting or susceptible to present a resistance to immunotherapy or to an anti-angiogenic agent, in particular to an anti-VEGF treatment.

In a particular embodiment, subjects according to the invention are subjects suffering from a solid tumor cancer selected from lung cancer (small cell and non-small cell), breast cancer, ovarian cancer, cervical cancer, uterus cancer, head and neck cancer, melanoma, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer, in particular glioblastoma.

In a particular embodiment, subjects according to the invention are subjects suffering from a solid tumor cancer and have high α-smooth muscle actin (α-SMA) expression.

In another particular embodiment, subjects according to the invention are subjects suffering from hepatocellular carcinoma (HCC).

In another particular embodiment, subjects according to the invention are subjects suffering from head and neck tumors.

In another particular embodiment, subjects according to the invention are subjects suffering from melanoma.

In another particular embodiment, subjects according to the invention are subjects suffering from colon cancer.

In another particular embodiment, subjects according to the invention are subjects suffering from lung carcinoma.

In another particular embodiment, subjects according to the invention are subjects suffering from breast cancer.

In another particular embodiment, subjects according to the invention are subjects suffering from hepatocellular carcinoma or hepatic cancer.

In another particular embodiment, subjects according to the invention are subjects suffering from rectal cancer or colorectal carcinoma.

In another particular embodiment, subjects according to the invention are subjects suffering from kidney cancer.

In another particular embodiment, subjects according to the invention are subjects suffering from pancreatic cancer.

In another particular embodiment, subjects according to the invention are subjects suffering from brain cancer, in particular glioblastoma.

In another particular embodiment, subjects according to the invention are subjects with solid tumor cancer who are at risk of developing resistance or partial resistance to anti-cancer immunotherapy due to another concomitant treatment or a genetic pre-disposition.

In another particular embodiment, subjects according to the invention are subjects with haematological malignancies such as lymphomas or leukaemias.

Use According to the Invention

In a particular embodiment, the invention provides compounds, methods, uses and compositions useful for the treatment of a solid tumor cancer in the form of a combination wherein at least one NOX4/1 inhibitor is to be administered in combination with at least one anti-cancer immunotherapeutic agent.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

The efficacy of NOX4/1 inhibitors for restoring or increasing responsiveness to an anti-cancer immunotherapeutic agent can be tested as follows:

Example 1: Combination of NOX4/1 Inhibitors and an Anti-PD1 Inhibitor in the Treatment of Cancer In order to test the efficacy of a combination according to the invention, the following experiments are conducted in a mouse xenograft tumour models as described below.

Subcutaneous xenograft tumours composed of C38 cells (colon cancer), CT26 cells (colon cancer), LLC1 cells (lung carcinoma), B16F10 cells (melanoma), Hepa1-6 cells (liver cancer) or Renca cells (renal cancer) are injected subcutaneously into the flank of C57Bl/6 or Balb/c mice (2-3 months old). Alternatively, MC-38 Cell Line derived from C57BL6 murine colon adenocarcinoma cells or Mouse 4T1 breast tumor model are used.

The combined treatment starts when the tumours reach a mean volume of 80-200 mm$^3$. Mice are randomized according to their individual tumour volume into different groups of 8 to 17 mice. Each group receives either placebo, or a NOX4/1 inhibitor alone, or a PD-1 antibody alone or NOX4/1 in combination with PD-1 antibody.

The NOX4/1 inhibitors 2-(2-chlorophenyl)-4-[3-(dimethylamino)phenyl]-5-methyl-1H-pyrazolo[4,3-c]pyridine-3,6(2H,5H)-dione or (R)-3-methoxy-4-(2-morpholino-1-phenylethoxy)-N-(5-(pyridin-4-yl)-1,3,4-thiadiazol-2-yl) benzamide are prepared daily (7 days/week) in 1.2% Methyl cellulose plus 0.8% Polysorbate80 (Sigma) and are administered in the animals from the respective groups by oral gavage via gavage tube at a 60 and 10 mg/kg dose respectively.

As PD-1 inhibitor, an anti-PD-1 antibody (ref.: BE0146, BioXcell; clone: RMP1-14, reactivity: mouse; isotype: Rat IgG2a; storage conditions: +4° C.) is injected into the peritoneal cavity of mice (Intraperitoneally, IP). The administration volume is 10 mL/Kg adjusted to the most recent individual body weight of mice.

Tumor Collection and Immunochemistry to Assess T-Cell Infiltration

Fourteen (14) days after randomization and if the antitumor activity of NOX4/1 compounds alone or in combination is considered sufficient, tumors from 5 satellite mice per group are collected, weighed and the tumor is cut in 2 fragments. One fragment is cut into slices 4 mm thick and fixed in 4% neutral buffered formalin for 24 to 48 h, and then embedded in paraffin (Histosec®, Merck, Darmstadt, Germany). One fragment is embedded in tissue Freezing Medium (Microm Microtech, France), snap-frozen in isopentane cooled over liquid nitrogen and stored at 80° C. until processing. Immunohistochemical stains for CD3, CD4 and CD8 are performed on paraffin-embedded tissue sections using standard techniques (Biodoxis, France). The number of CD3, CD4 and CD8 immunopositive cells per field are counted.

Tumor Collection and Flow Cytometry to Assess T-Cell Infiltration

Fourteen days after randomization, the tumour from 4 mice per group are collected.

All the tumours are collected in RPMI culture medium (ref: BE12-702F, Lonza, Verviers, Belgium). The tumour immune infiltrate cells are quantified by flow cytometry analysis from each collected sample. Then, the antibodies directed against the chosen markers are added, according to the procedure described by the supplier for each antibody. All the antibodies except FoxP3 will be for surface labeling and FoxP3 for intracellular labeling. The antibodies used for flow cytometry analysis for effector T-Cell lymphocytes (Teff: CD45, CD3, CD8) and regulatory T-Cell lymphocytes (Treg: CD45, CD3, CD4, FoxP3) on mouse samples are listed in the Table 1 below:

TABLE 1

| Specificity and fluorochrome | | Reference | Provider | Isotype and fluorochrome | | Reference of isotype | Provider |
|---|---|---|---|---|---|---|---|
| CD45 | APC-Cy7 | 557659 | BD Biosciences | Rat IgG2bk | APC-Cy7 | 552773 | BD Biosciences |
| CD3 | V450 | 561389 | BD Biosciences | rat IgG2bk | V450 | 560457 | BD Biosciences |
| CD8 | PerCP | 553036 | BD Biosciences | Rat IgG2ak | PerCP | 553933 | BD Biosciences |
| FoxP3 | PE | 130-093-014 | Miltenyi Biotec | | PE | | |
| CD4 | Viogreen | 130-102-444 | Miltenyi Biotec | IgG2b | Viogreen | 130-102-659 | Miltenyi Biotec |

The stained cells are analyzed with a BD™ LSR II flow cytometer (BD Biosciences) equipped with 3 excitation lasers at wavelengths 405, 488 and 633 nm. Flow cytometry data is acquired until either 10,000 mCD45+ events are recorded for each sample, or for a maximum duration of 2 minutes.

Animal Monitoring

All study data, including animal body weight measurements, tumor volume, clinical and mortality records, and treatment is scheduled and recorded. The viability and behavior is recorded every day. Body weights are measured twice a week. The length and width of the tumor is measured twice a week with calipers and the volume of the tumor is estimated by the formula:

$$\text{Tumor volume} = \frac{\text{width}^2 \times \text{length}}{2}$$

Humane endpoints. Experiment is terminated after 5 weeks or if:
Tumor exceeding 10% of normal body weight or exceeding 1,500 mm³ in mice,
Tumors interfering with ambulation or nutrition, >8 mm ulcerated tumor, infection of bleeding,
Tissue erosion,
20% body weight loss remaining for 2 monitoring days (30% for one monitoring day) compared to treatment initiation day/maximum weight,
Signs of pain, suffering or distress: pain posture, pain face mask, behavior,
Poor body condition, emaciation, cachexia, dehydration,
Prolonged absence of voluntary responses to external stimuli,
Rapid labored breathing, anemia, significant bleeding,
Neurologic signs: circling, convulsion, paralysis,
Sustained decrease in body temperature,
Abdominal distension.

Efficacy Parameters

The treatment efficacy is assessed in terms of the effects of the test substances on the tumor volumes of treated animals relative to control animals. The following evaluation criteria of antitumor efficacy are determined.
Individual and/or mean (or median) tumor volumes will be provided,
Tumor doubling time (DT) will be calculated,
Tumor growth inhibition (T/C %) defined as the ratio of the median tumor volumes of treated versus control group will be calculated:

$$T/C\% = \frac{\text{Median tumor volume of treated group at } DX}{\text{Median tumor volume of vehicle treated group at } DX} \times 100$$

The optimal value is the minimal T/C % ratio reflecting the maximal tumor growth inhibition achieved. The effective criteria for the T/C % ratio according to NCI standards, is * 42%. Volume V and time to reach V is calculated. Volume V is defined as a target volume deduced from experimental data and chosen in exponential phase of tumor growth. For each tumor, the closest tumor volume to the target volume V is selected in tumor volume measurements. The value of this volume V and the time for the tumor to reach this volume is recorded. For each group, the mean of the tumor volumes V and the mean of the times to reach this volume is calculated. Mice survival will also be monitored and used as an efficacy parameter. Survival curves are drawn.

When MC38 cancer cells (0.5×105) are used, those are injected in phosphate-buffered saline (PBS) subcutaneously (s.c) into the flank of C57BL/6 female mice aged 8-10 weeks. MC38 cells are either injected on their own, or mixed with C57BL/6 colon fibroblasts (2.5×105), pre-treated ex vivo prior to injection with 2 ng/ml of TGFβ1 for 6 days to induce a CAF phenotype.

When 4T1 cancer cells (0.5×105) are used, those are injected in PBS s.c into the upper mammary fat pad of female mice aged 8-10 weeks. Cells are either injected on their own, or mixed with 2.5×105 BALB/C breast CAFs isolated from transgenic BALBneuT spontaneous stromal-rich breast tumours.

The NOX4 inhibitor 2-(2-chlorophenyl)-4-[3-(dimethylamino)phenyl]-5-methyl-1H-pyrazolo [4,3-c]pyridine-3,6 (2H,5H)-dione (GKT137831) was administered to mice when tumours were palpable. GKT137831 was reconstituted in 1.2% Methyl Cellulose (Sigma) with 0.1% Polysorbate (Sigma) and administered by oral gavage 5×/week at 40 mg/kg. Control mice received vehicle by oral gavage. For longer term dosing, 15 initial doses were given as stated, but reduced to 3×/week for 3 weeks at 50 mg/kg, then 2×/week for 3 weeks at 60 mg/kg. The anti PD-1 antibody (Bioxcell; RMP1-14) was given via intraparietal (i.p) injection. 300 µg of the antibody or the IgG2a isotype control (Bioxcell) were given when tumours were palpable every other day, totaling 3 doses.

Figure 1B:
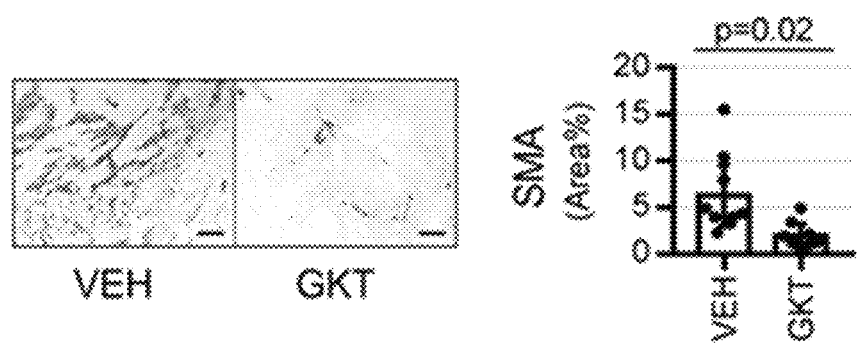
Figure 1C:
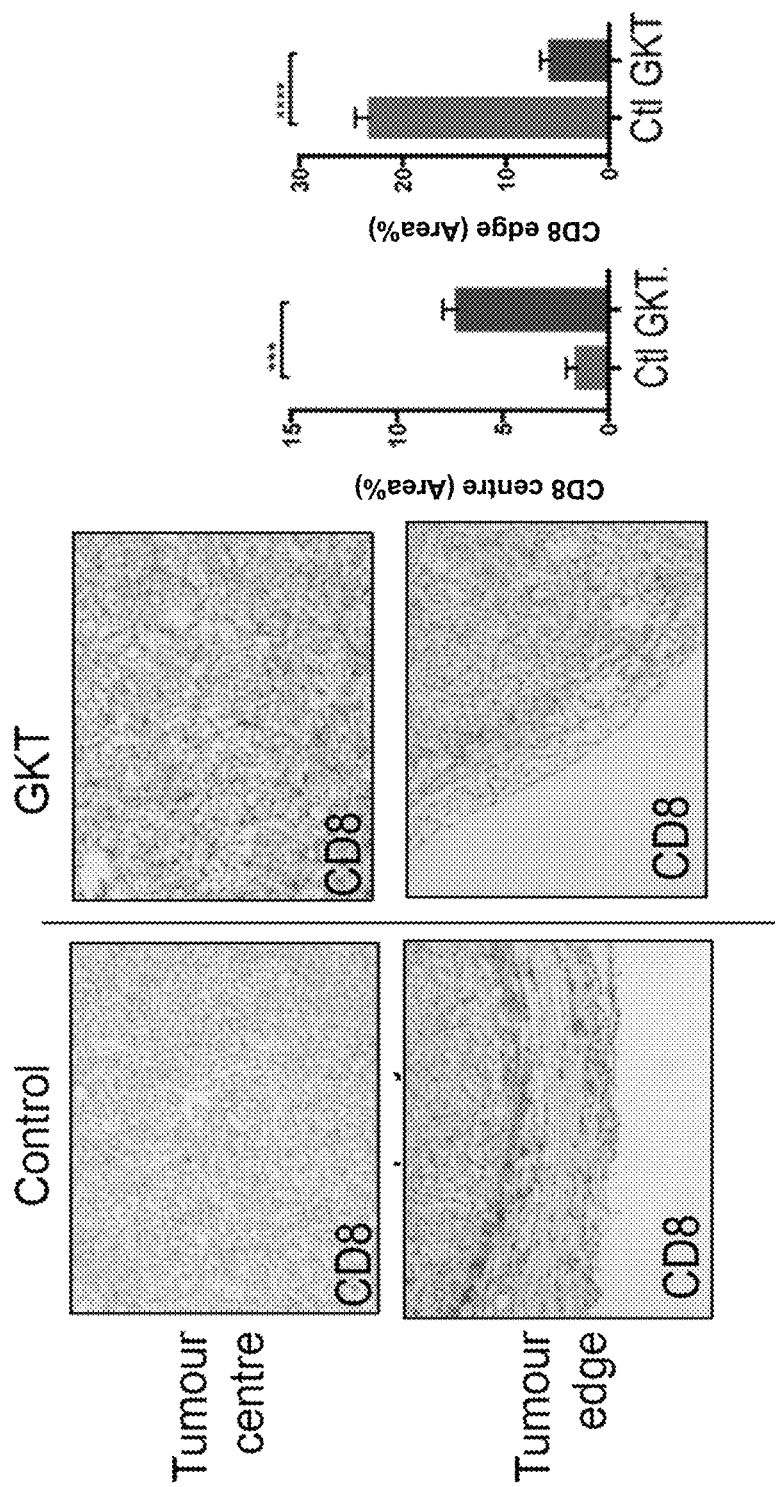

For the data presented under FIG. 1, tumours were measured every 2-3 days by electronic skin caliper from longest width and length. Tumour volume was calculated using the formula 4/3πXr3, where the radius (r) was calculated from tumour width and length measurement to provide an average diameter value. Mice were randomized into groups based on tumour volume so that no statistical difference occurred between mean tumour volumes between groups before treatments began. FIG. 1A shows that at day 15 i.e. after 8 days of treatment, tumours were significantly smaller when mice were treated with the NOX4 inhibitor than compared with vehicle alone. Further, since immunochemistry (carried out as described above) revealed, as represented on FIGS. 1B and 1C, respectively, that the treatment with the NOX4 inhibitor significantly reduces SMA-positive CAF in tumours and results in relocation of CD8+ T-cells from the tumour edge into the centre of the tumour. Using the 4T1 breast cancer model, these results clearly show that treatment with GKT inhibits formation of CAFs as shown by the diminished myobibroblast (SMA-positive cells) population, allowing CD8⁺ T-cells access to the tumour and kill cancer cells, reducing the tumour size. It supports the beneficial effects of the combination of a NOX4 inhibitor and anti-cancer immunotherapeutic agent that would further activate the CD8⁺ T-cells.

Figure 2A:
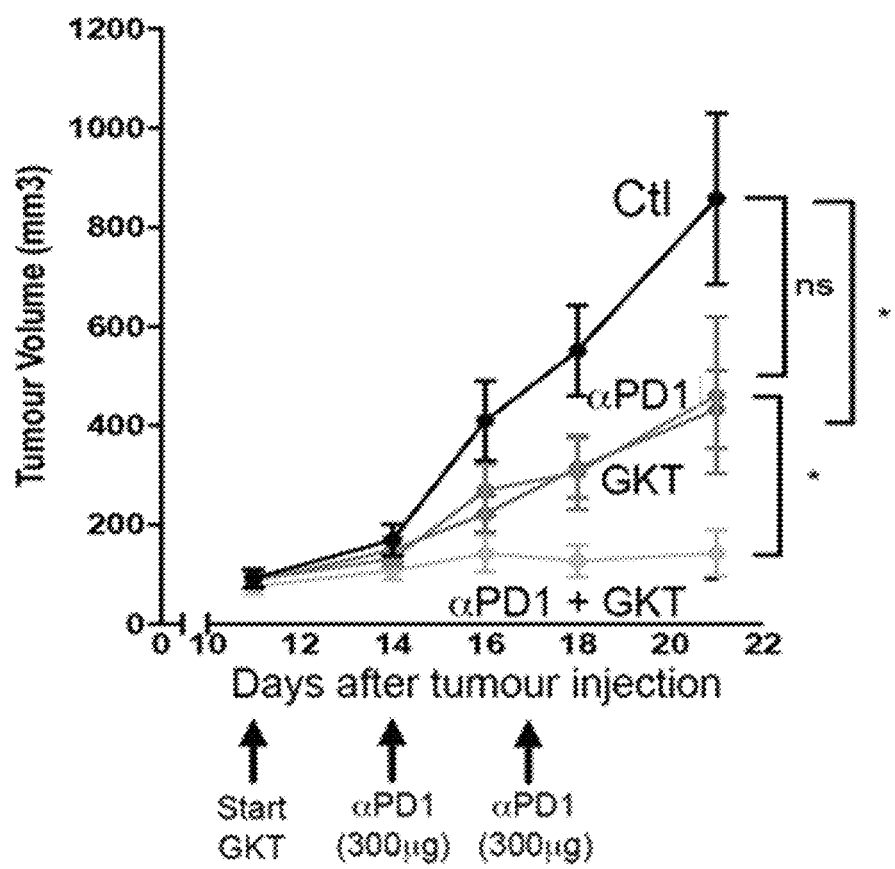
FIG. 2 shows the effects of a combination of αPD1 with a NOX4 inhibitor (GKT) on the therapeutic response in CAF-rich tumours where MC38 cancer cells were co-injected with cancer-associated fibroblasts (CAF) in mice which are treated as described in Example 1 and effects of a vehicle alone (Ctl), αPD1, NOX4 inhibitor (GKT) alone or a combination αPD1+ NOX4 inhibitor (GKT) are compared in terms of tumour growth after injection (A); B: Immunochemistry and quantification thereof showing that treatment with the combination αPD1/NOX4 inhibitor results in relocation of CD8+ T-cells from the tumour edge into the centre of the tumour compared to αPD1 alone; C: Kaplan Meier survival curves in the various groups.
Figure 2B:
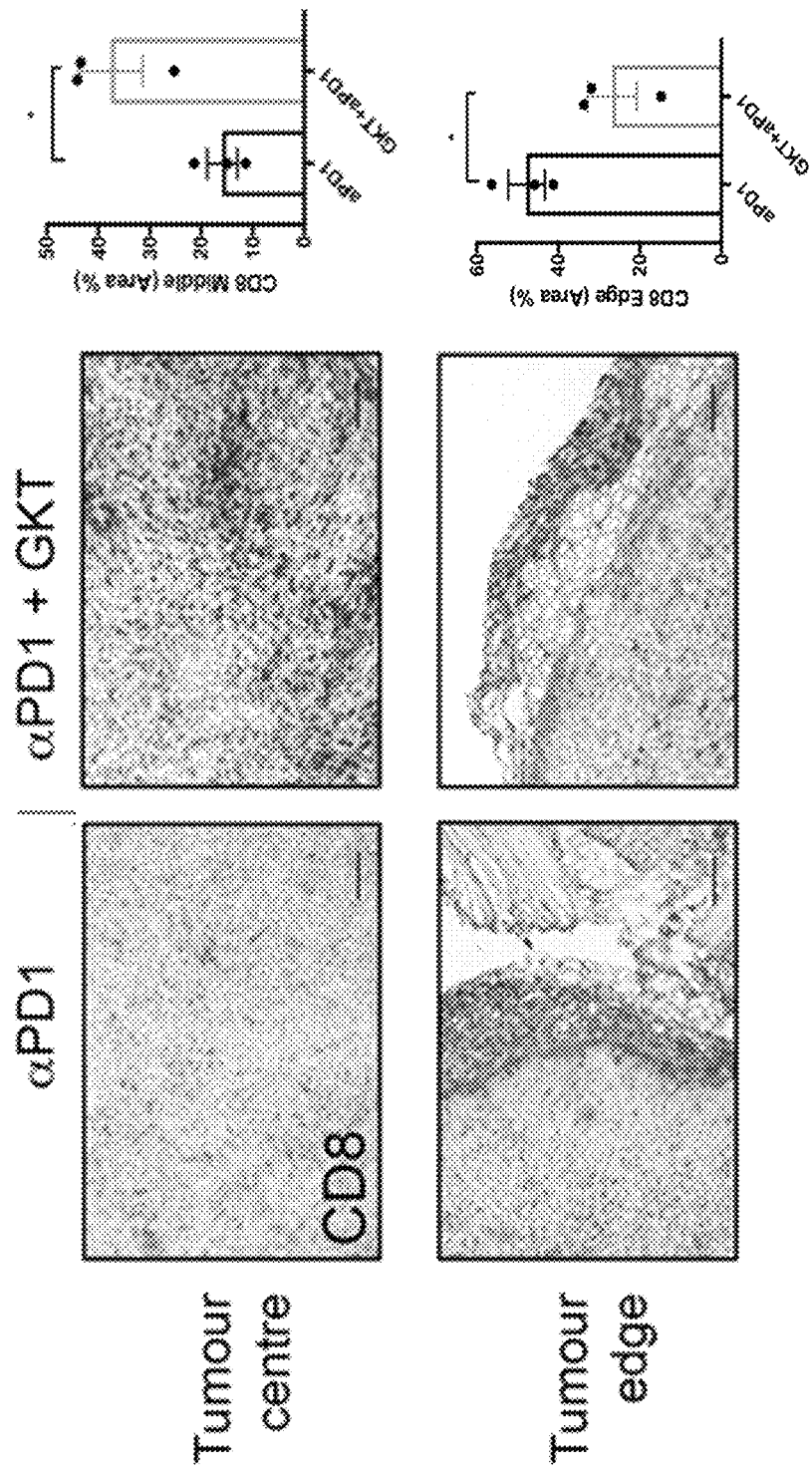
Figure 2C:
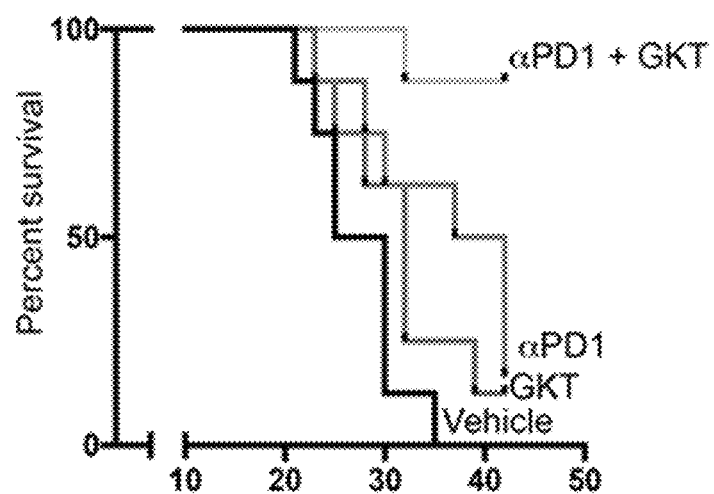

The beneficial effects of such a combination is further supported by the results presented on FIG. 2 for the combination of a PD-1 inhibitor (αPD1) with the NOX4 inhibitor GKT137831 which significantly improves therapeutic response in CAF-rich tumours: tumours were significantly smaller when mice were treated with αPD1/GKT831 combination compared with αPD1 alone (FIG. 2A) and following the administration of the αPD1/GKT831 combination, there is a significant relocation of CD8+ T-cells from the tumour edge into the centre of the tumour (FIG. 2B) and the survival outcome is also significantly increased (FIG. 2C), compared with αPD1 alone. Using the MC38 colon cancer model, the beneficial effect of GKT/αPD1 combination therapy was confirmed by showing a very significant decrease of tumour volume, which is accompanied by an increase in mouse survival. Moreover, it was shown that this effect results from an infiltration of CD8+ T-cells into the tumour of the NOX inhibitors. These results strongly suggest that the NOX4 inhibitors of the invention, in particular GKT137831, are strong candidates for PD1 co-therapy for all CAF-rich cancers.

Example 2: Combination of NOX4/1 Inhibitors and a Cancer Vaccine in the Treatment of Cancer In order to test the efficacy of a combination according to the invention, NOX4/1 inhibitors are combined with the treatment with a vaccine such as an anti-HPV vaccine.

TC1 cancer cells ($0.5 \times 10^5$) (prostate cancer) were injected in phosphate-buffered saline (PBS) subcutaneously (s.c) into the flank of C57BL/6 female mice aged 8-10 weeks. TC1 cells were either injected on their own, or mixed with C57BL/6 lung fibroblasts ($2.5 \times 10^5$), pre-treated ex vivo prior to injection with 2 ng/ml of TGFβ1 for 6 days to induce a CAF phenotype.

Tumours were measured every 2-3 days by electronic skin caliper from longest width and length. Tumour volume measurements, mice randomized and oral gavage dosage were carried out as described above.

Vaccination with a DNA vaccine encoding tetanus Fragment C domain 1 (Dom) fused to the immunodominant CD8 epitope of E7 HPV RAHYNIVTF (RAH, E7$_{49-57}$) (Rice et al. 2002, *J Immunol.*, 169:3908-13; Rice et al., 2008, *Nat Rev Cancer*, 8:108-20) was administered via intramuscular injection (i.m) when tumours were palpable. One injection containing 50 μg of DNA in PBS was given and any repeat doses were given 3 weeks post initial immunization. Treatment with a NOX4 inhibitor (GKT137831) reconstituted as described in Example 1, was administered to mice when tumours were palpable.

Figure 3A:
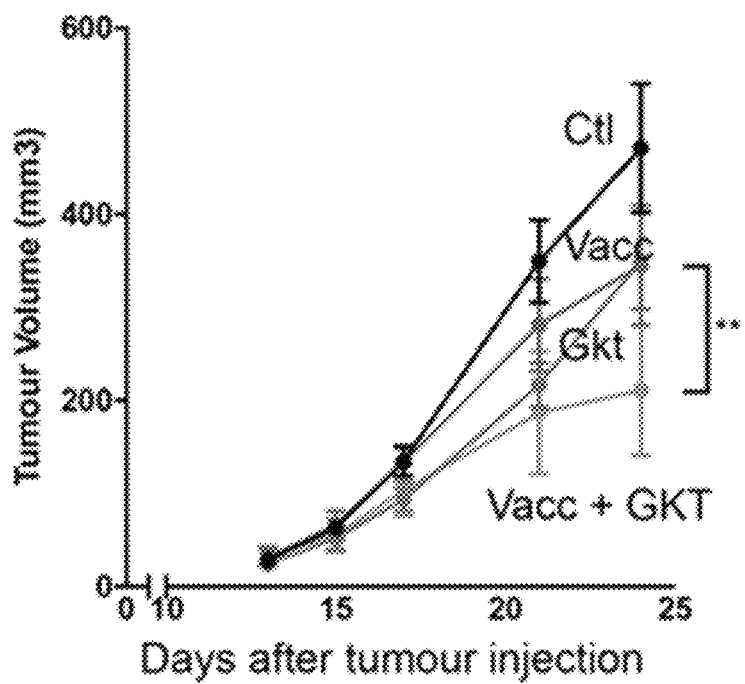
FIG. 3 shows the effects of a combination of an anti-tumour vaccination with a NOX4 inhibitor (GKT) as described in Example 2. A: Tumour growth after injection in mice treated with a combination vaccine/GKT compared with vaccine alone and controls; B: Immunochemistry and quantification thereof showing that treatment with the combination vaccine/NOX4 inhibitor results in relocation of CD8+ T-cells from the tumour edge into the centre of the tumour compared to vaccine alone; C: Kaplan Meier survival curves in the various groups.
Figure 3B:
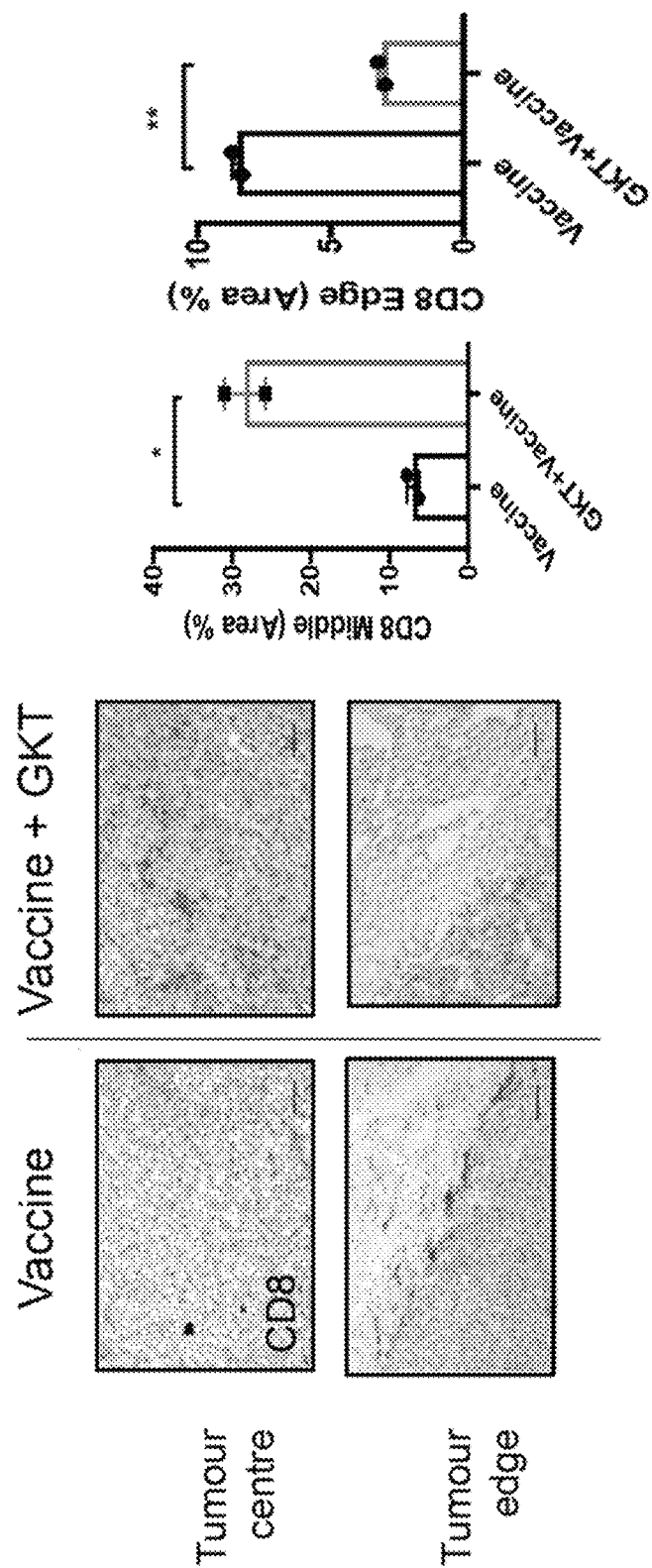
Figure 3C:
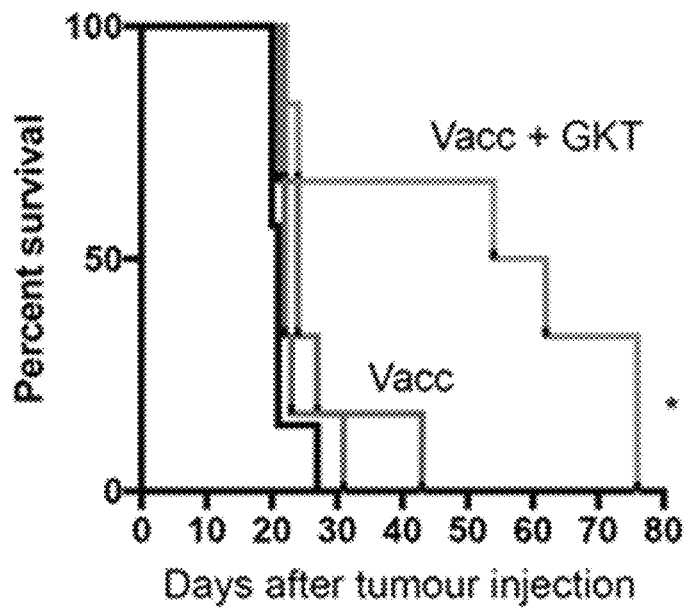

FIG. 3 supports that the combination of an anti-tumour vaccination with a NOX4 inhibitor significantly improves therapeutic response in CAF-rich tumours since at day 24, tumours were significantly smaller when mice were treated with the combination vaccine/NOX4 inhibitor compared with the vaccine alone and following the administration of the combination vaccine/NOX4 inhibitor, there is a significant relocation of CD8+ T-cells from the tumour edge into the centre of the tumour (FIG. 3B) and the survival outcome is also significantly increased (FIG. 3C), compared with vaccine alone. Effective immunotherapy, whether based on checkpoint inhibitors, T-cell agonists, vaccination or adoptive T-cell transfer, requires the presence of CD8+ effector T-cells in the tumour. Cancer-associated fibroblasts are found in most solid cancers, and play a major role in tumour immune evasion by excluding CD8+ T-cells from cancers, thereby rendering immunotherapies ineffective. Therefore, since NOX inhibitors of the invention, in particular GKT831, effectively target CAF as shown by the diminution of SMA-positive cells in the 4T1 model, it promotes CD8+ T-cell infiltration into tumours and restores response to vaccine-based and PD1-based immunotherapies. These data suggest that combination immunotherapy with NOX4 inhibitors of the invention, in particular GKT137831, may significantly improve response rates for this type of treatment.

Example 3: Combination of NOX4/1 Inhibitors and Anti-VEGF Agent in the Treatment of Cancer In order to test the efficacy of a combination according to the invention, NOX4/1 inhibitors are combined with the treatment with an anti-VEGF agent.

MC38 xenograft mouse models of tumors were produced by injecting MC38 tumor cells diluted in PBS ($5 \cdot 10^5$ for MC38) subcutaneously either in Wild-Type C57/BL6 mice or NOX1 deficient (NOX1-KO) mice. When tumors reached 50 mm³, intra-peritoneal administration of purified antibodies: either an anti-VEGF: DC101 or an irrelevant Rat IgG (as control) were performed twice a week. DC101 was given at a dose of 600 μg per injection per mouse. Vehicle (VL) (i.e. methylcellulose and Tween 80) or a NOX1-selective inhibitor, (R) 3-methoxy-4-(2-morpholino-1-phenylethoxy)-N-(5-(pyridin-4-yl)-1,3,4-thiadiazol-2-yl)benzamide (GKT2) (twice daily at 10 mg/kg) were given by oral gavage until the sacrifice of mice. Tumor size was measured with a caliper and tumor volume was determined according to the equation: (Length*width*thickness). Tumor size was measured in vivo by a caliper (D-0 to D-15) every 5 days. After sacrifice, tumors were removed without fixation with PFA (paraformaldehyde), isolated and blood vascular endothelial cells (CD45−/CD31+/GP38−) were analyzed by flow cytometry.

Figure 4:
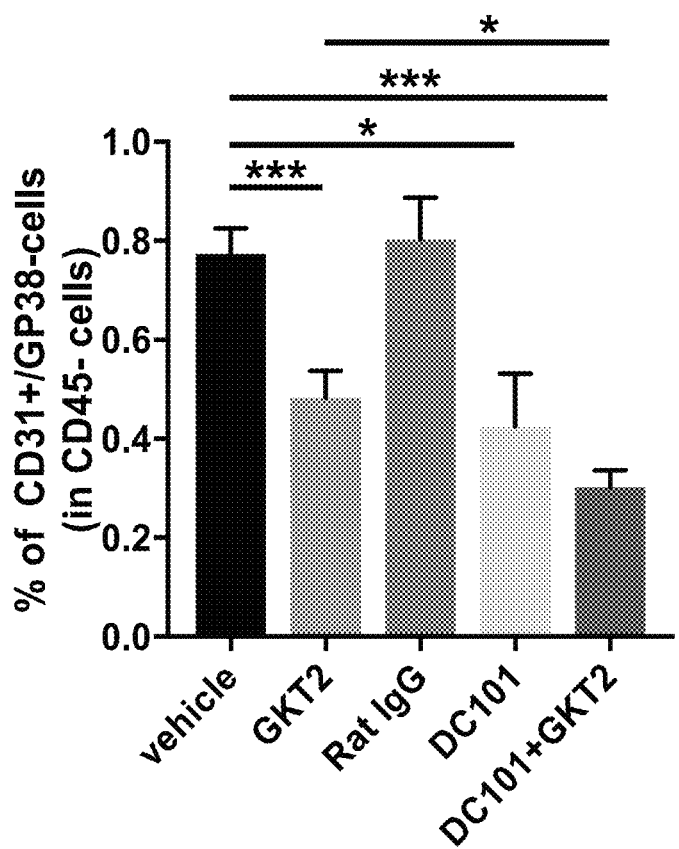
FIG. 4 shows the efficacy of the combination of an anti-angiogenic agent and a selective NOX1 inhibitor (GKT2) in inhibiting angiogenesis as measured by CD45−/CD31+/GP38− cells as described in Example 3 as compared to controls (*p<0.05; p<0.01; *p<0.005; ****p<0.001).

FIG. 4 shows that the combination of a highly selective NOX1 inhibitor (GKT2) and an anti-VEGF-R2 blocking antibody (DC101) allows inhibiting angiogenesis. Moreover, GKT2 and DC101 act synergistically in enhancing inhibition of neo-vascularization.

Figure 5:
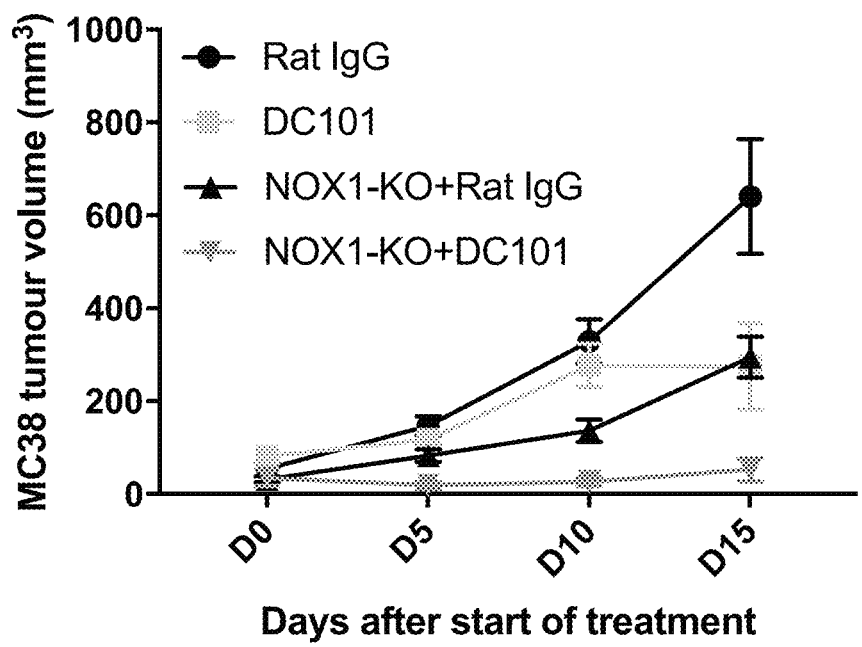
FIG. 5 shows tumor size growth in NOX1-KO mice as compared in WT mice and the effect of an anti-VEGFR2 antibody (DC101) in decreasing tumor growth in those mice.

FIG. 5 shows that tumors in NOX1-KO mice showed decreased growth kinetics as compared to tumors in WT mice indicating a clear involvement of NOX1. Further, treatment with the anti-VEGFR2 antibody (DC101) decreased tumor growth in NOX1 deficient mice and this effect was even more pronounced compared to WT mice. This clearly suggests different mechanisms of action between VEGFR2 and NOX1 signaling.

Therefore, altogether, those data support that the combination of NOX1 inhibition and anti-angiogenic agents such as anti-VEGF inhibitors would allow achieving a synergistic effect for tumor treatment.

The invention claimed is:

1. A method for treating a subject suffering from a solid tumor presenting resistance to a PD-1 inhibitor immunotherapy, said method comprising: administering an effective amount of 2-(2-chlorophenyl)-4-[3-(dimethylamino)phenyl]-5-methyl-1H-pyrazolo[4,3-c]pyridine-3,6(2H,5H)-dione in combination with the PD-1 inhibitor immunotherapy to a subject in need of treatment, wherein said administering is effective to treat the cancer presenting resistance to the PD-1 inhibitor immunotherapy.

2. The method according to claim 1, wherein the solid tumor is selected from the group consisting of lung cancer, breast cancer, ovarian cancer, cervical cancer, uterus cancer, head and neck cancer, melanoma, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer.

3. The method according to claim 1, wherein the solid tumor is esophageal cancer.

4. The method according to claim 1, wherein the PD-1 inhibitor is selected from Pembrolizumab and Nivolumab.

5. A method for restoring solid tumor sensitivity to immunotherapeutic treatment using a PD-1 inhibitor in a subject, said method comprising an effective amount of 2-(2-chlorophenyl)-4-[3-(dimethylamino)phenyl]-5-methyl-1H-pyrazolo[4,3-c]pyridine-3,6(2H,5H)-dione or pharmaceutical formulation thereof in combination with an immunotherapeutic treatment to a subject presenting resistance to the immunotherapeutic treatment, thereby restoring solid tumor sensitivity to the immune therapeutic treatment.

6. The method according to claim 2, wherein the brain cancer is glioblastoma.

7. The method according to claim 1, wherein the solid tumor is selected from the group consisting of lung cancer, head and neck cancer, and colon cancer.

8. The method according to claim 5, wherein the solid tumor is selected from the group consisting of lung cancer, breast cancer, ovarian cancer, cervical cancer, uterus cancer, head and neck cancer, melanoma, hepatocellular carcinoma, colon cancer, rectal cancer, colorectal carcinoma, kidney cancer, prostate cancer, gastric cancer, bronchus cancer, pancreatic cancer, urinary bladder cancer, hepatic cancer and brain cancer.

9. The method according to claim 8, wherein the brain cancer is glioblastoma.

10. The method according to claim 5, wherein the solid tumor is selected from the group consisting of lung cancer, head and neck cancer, and colon cancer.

11. The method according to claim 5, wherein the solid tumor is esophageal cancer.

12. The method according to claim 5, wherein the PD-1 inhibitor is selected from Pembrolizumab and Nivolumab.

\* \* \* \* \*

UNITED STATES PATENT AND TRADEMARK OFFICE
CERTIFICATE OF CORRECTION

| | | |
|---|---|---|
| PATENT NO. | : 12,011,436 B2 | Page 1 of 1 |
| APPLICATION NO. | : 16/760910 | |
| DATED | : June 18, 2024 | |
| INVENTOR(S) | : Philippe Wiesel | |

It is certified that error appears in the above-identified patent and that said Letters Patent is hereby corrected as shown below:

In the Claims

In Claim 5, at Column 29, Line 1, please insert -- administering -- after "comprising".

Signed and Sealed this
Twenty-fourth Day of December, 2024

Derrick Brent
*Acting Director of the United States Patent and Trademark Office*